(12) United States Patent
Choi et al.

(10) Patent No.: US 12,257,280 B2
(45) Date of Patent: Mar. 25, 2025

(54) **COMPOSITION FOR PREVENTING OR TREATING MUSCULAR DISEASES, CONTAINING, AS ACTIVE INGREDIENT, *GLYCYRRHIZA URALENSIS* EXTRACT OR COMPOUND ISOLATED THEREFROM**

(71) Applicant: NEO CREMAR CO., LTD., Seoul (KR)

(72) Inventors: Inho Choi, Gyeongsan-si (KR); Eun Ju Lee, Daegu (KR); So-young Park, Daegu (KR); Yong-Ho Lee, Daegu (KR); Jin Yeul Ma, Daejeon (KR); Won-Kyung Cho, Daegu (KR); Hye Jin Yang, Daejeon (KR)

(73) Assignee: NEO CREMAR CO., LTD., Seoul (KR)

( * ) Notice: Subject to any disclaimer, the term of this patent is extended or adjusted under 35 U.S.C. 154(b) by 653 days.

(21) Appl. No.: 17/266,610

(22) PCT Filed: Jun. 17, 2020

(86) PCT No.: PCT/KR2020/007826
§ 371 (c)(1),
(2) Date: Feb. 7, 2021

(87) PCT Pub. No.: WO2020/256397
PCT Pub. Date: Dec. 24, 2020

(65) Prior Publication Data
US 2021/0315957 A1  Oct. 14, 2021

(30) Foreign Application Priority Data

| Jun. 19, 2019 | (KR) | ......................... | 10-2019-0072992 |
| Jun. 16, 2020 | (KR) | ......................... | 10-2020-0073088 |
| Jun. 16, 2020 | (KR) | ......................... | 10-2020-0073089 |
| Jun. 16, 2020 | (KR) | ......................... | 10-2020-0073090 |
| Jun. 16, 2020 | (KR) | ......................... | 10-2020-0073091 |
| Jun. 16, 2020 | (KR) | ......................... | 10-2020-0073092 |

(51) Int. Cl.
| *A61K 36/484* | (2006.01) |
| *A23L 33/00* | (2016.01) |
| *A23L 33/105* | (2016.01) |
| *A61K 9/00* | (2006.01) |
| *A61K 31/12* | (2006.01) |
| *A61K 31/353* | (2006.01) |
| *A61P 21/00* | (2006.01) |

(52) U.S. Cl.
CPC .......... *A61K 36/484* (2013.01); *A23L 33/105* (2016.08); *A23L 33/40* (2016.08); *A61K 9/0056* (2013.01); *A61K 31/12* (2013.01); *A61K 31/353* (2013.01); *A61P 21/00* (2018.01); *A23V 2002/00* (2013.01); *A61K 2236/331* (2013.01); *A61K 2236/333* (2013.01)

(58) Field of Classification Search
None
See application file for complete search history.

(56) References Cited

FOREIGN PATENT DOCUMENTS

| CN | 109890378 A | 6/2019 |
| JP | 2009-143838 A | 7/2009 |
| JP | 2012-193157 A | 10/2012 |
| JP | 2015-232004 A | 12/2015 |
| JP | 6010665 B | 10/2016 |
| KR | 10-2006-0039036 A | 5/2006 |
| KR | 10-2010-0014124 A | 2/2010 |
| KR | 10-2010-0101848 A | 9/2010 |
| KR | 10-2010-0135424 A | 12/2010 |
| KR | 10-2011-0098994 A | 9/2011 |
| KR | 10-2012-0005111 A | 1/2012 |
| KR | 10-2017-0132475 A | 12/2017 |
| WO | 2018-079715 A1 | 5/2018 |

OTHER PUBLICATIONS

Ilaria Paterni et al., "Estrogen receptors alpha (ERα) and beta (ERβ): Subtype-selective ligands and clinical potential", Steroids, vol. 90, Nov. 15, 2014, pp. 13-29.
RyunosukeTanemoto et al., "The constituents of licorice (*Glycyrrhiza uralensis*) differentially suppress nitric oxide production in interleukin-1β-treated hepatocytes", Biochemistry and Biophysics Reports, vol. 2, Jul. 2015, pp. 153-159.
Tianbao Chen et al., "The inhibitory effect of Isoliquiritigenin on the proliferation of human arterial smooth muscle cell", BMC Pharmacology and Toxicology, vol. 18, No. 1, Jul. 17, 2017, pp. 1-8.
Eun Ju Lee et al., "Isolation and Characterization of Compounds from Glycyrrhiza uralensis as Therapeutic Agents for the Muscle Disorders", IInternational Journal of Molecular Sciences, vol. 22, No. 2, Jan. 1, 2021, p. 876.
International Search Report for PCT/KR2020/007826 mailed Oct. 8, 2020 from Korean Intellectual Property Office.

Primary Examiner — Susan Hoffman
(74) Attorney, Agent, or Firm — Revolution IP, PLLC

(57) ABSTRACT

A pharmaceutical composition and a health functional food composition for preventing, treating, or improving muscular diseases have licorice extract or a fraction thereof, or a compound isolated therefrom or a pharmaceutically acceptable salt thereof, as an active ingredient. The licorice extract or a fraction thereof, the compound or salt thereof induce the myoblasts proliferation and promote the differentiation into myotubes, and since the licorice extract or a fraction thereof, the compound or salt thereof has an excellent effect on regenerating damaged muscles, various muscle diseases are effectively prevented, improved or treated using the composition.

7 Claims, 8 Drawing Sheets
Specification includes a Sequence Listing.

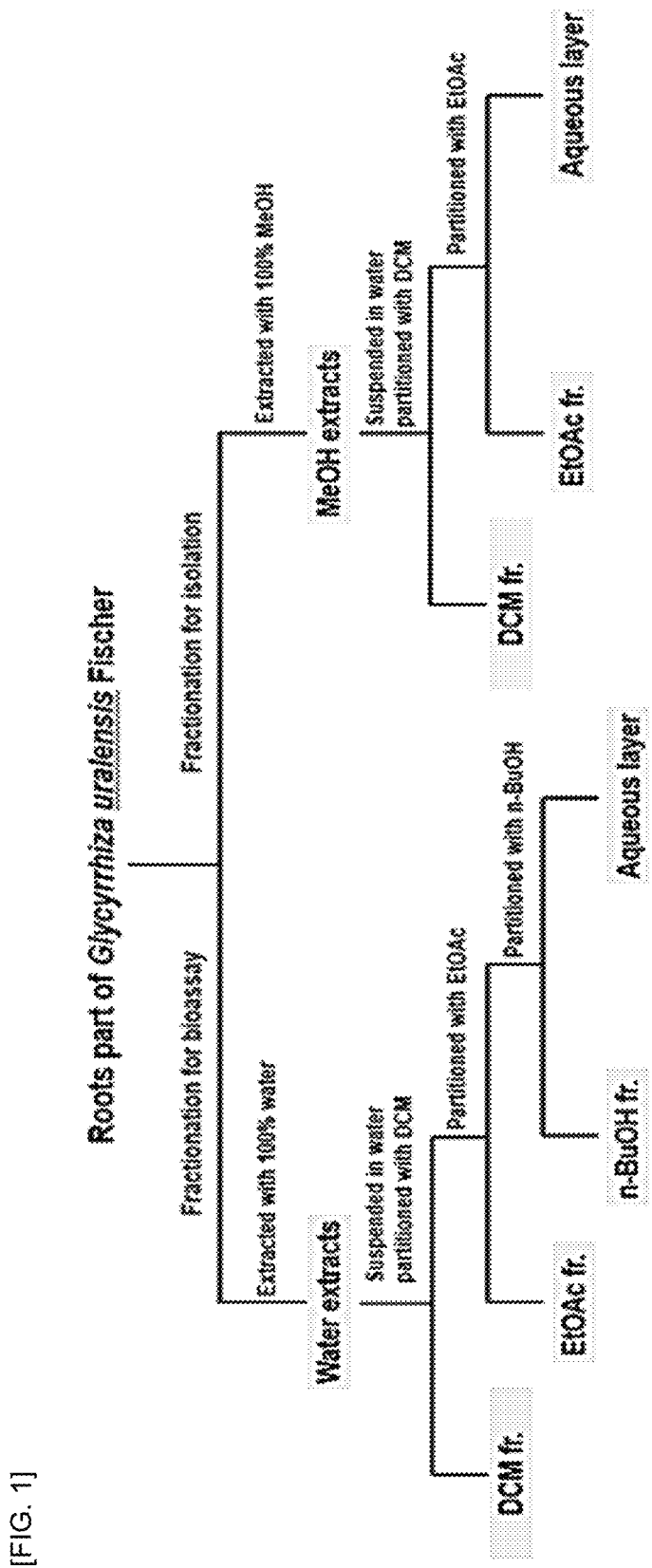
[FIG. 1]

[FIG. 2]
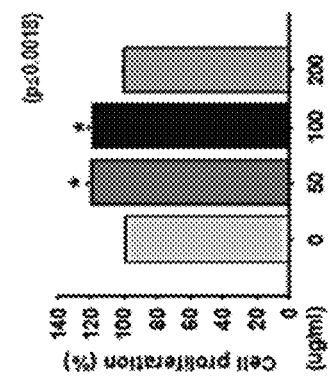
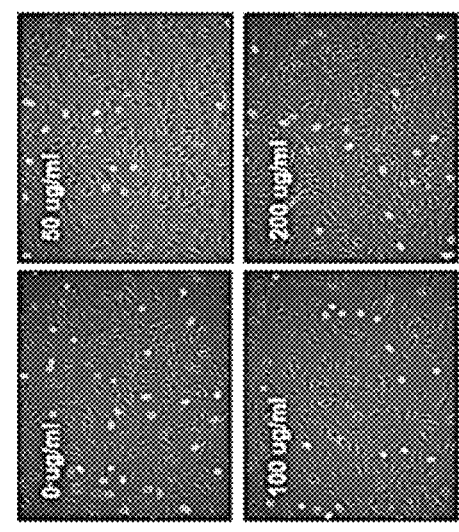
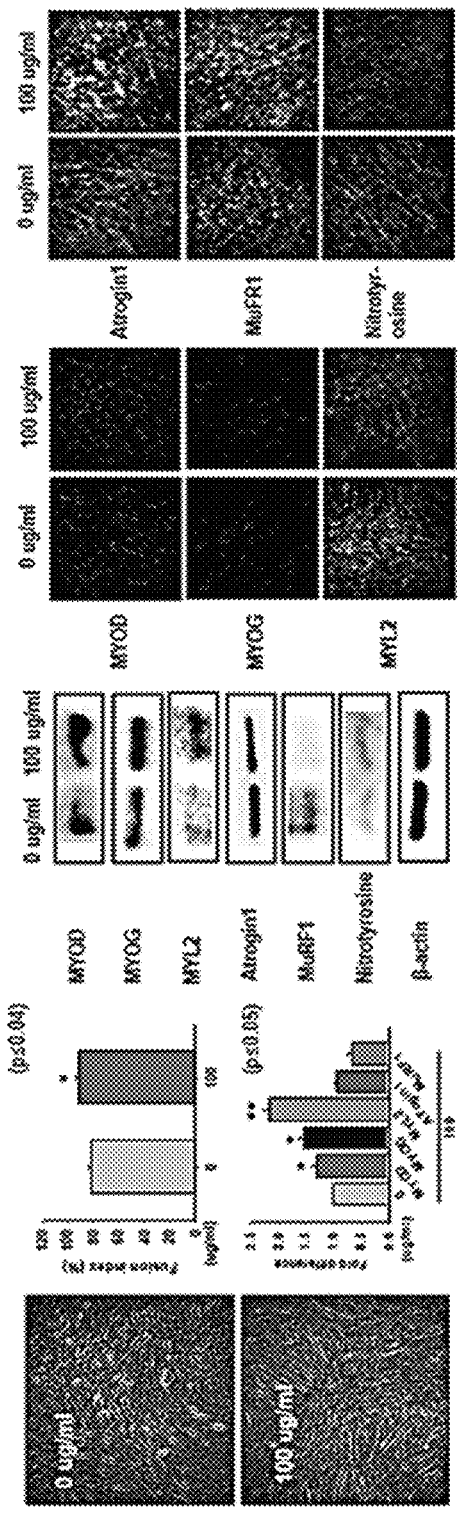

[FIG. 3]
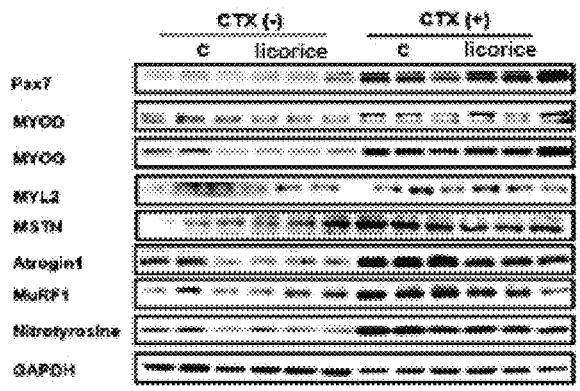
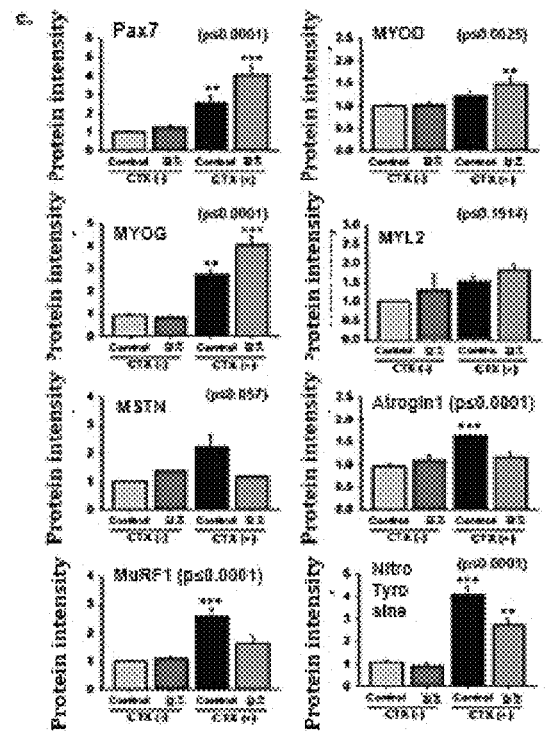
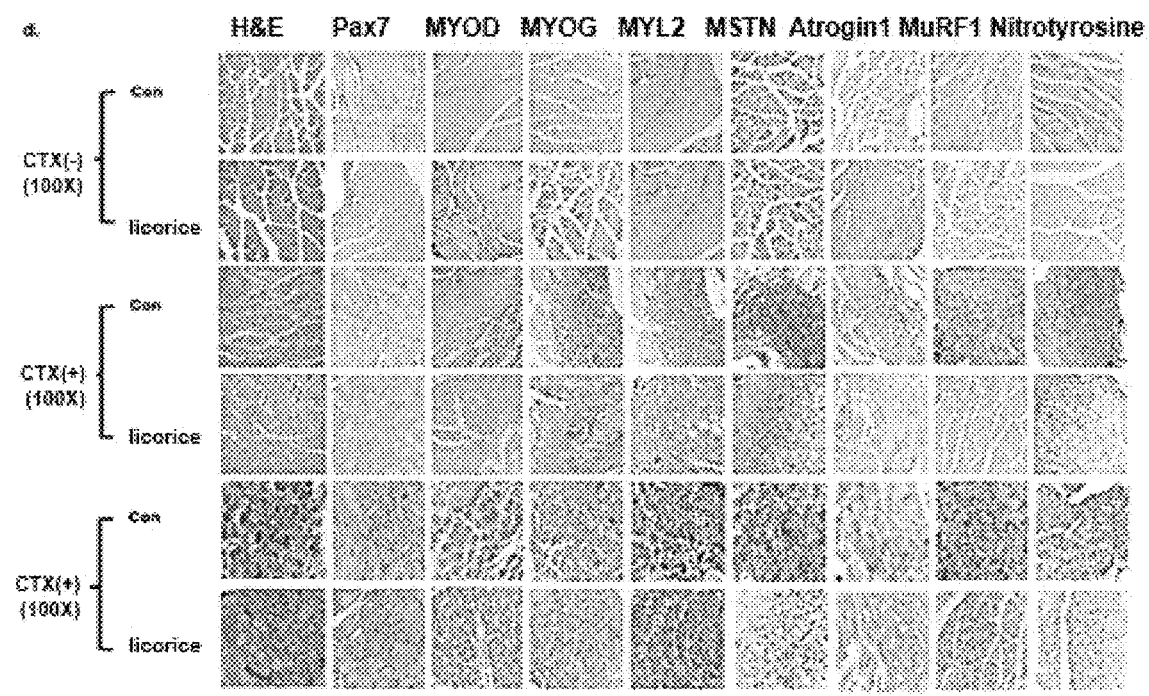

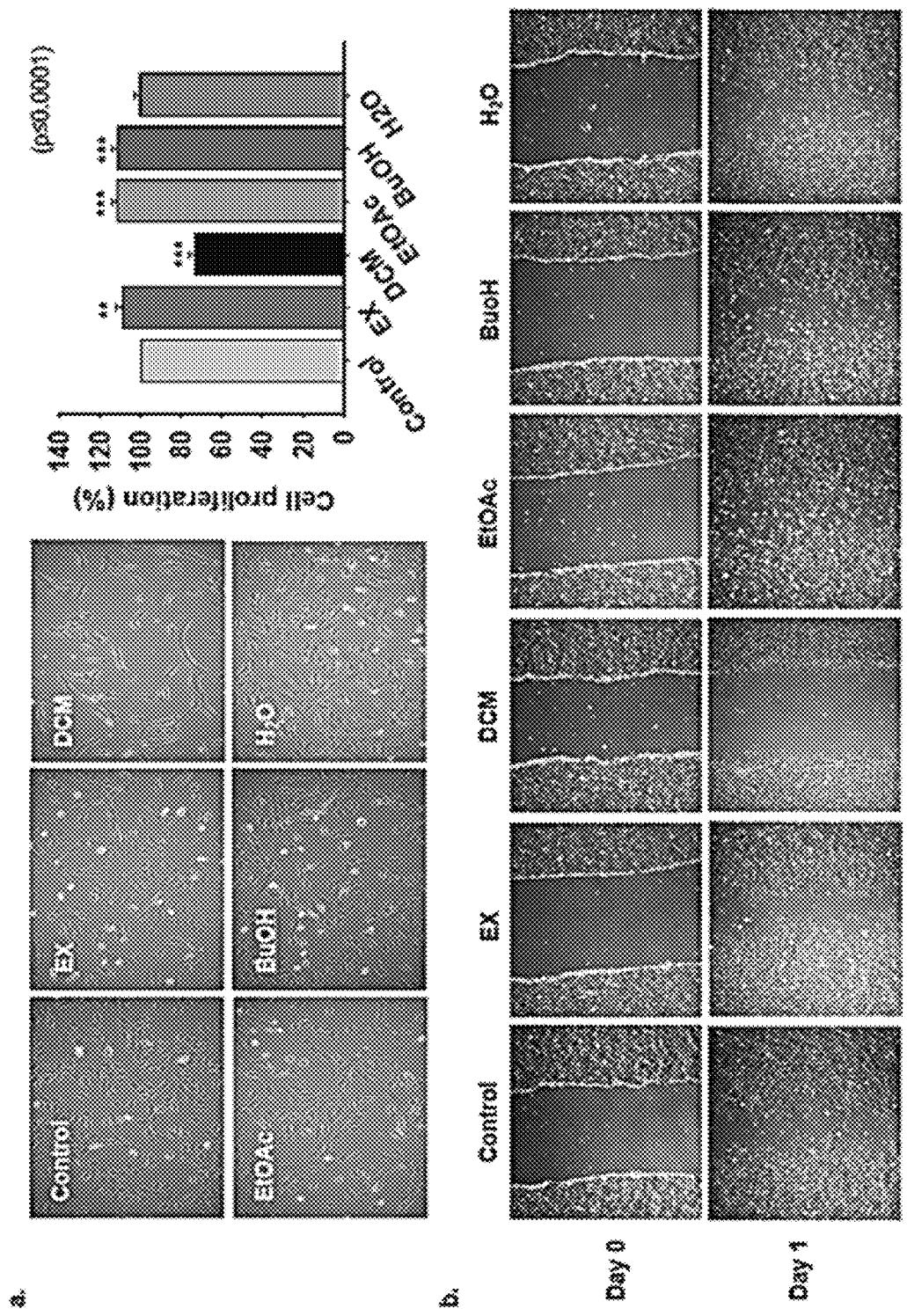
[FIG. 4]

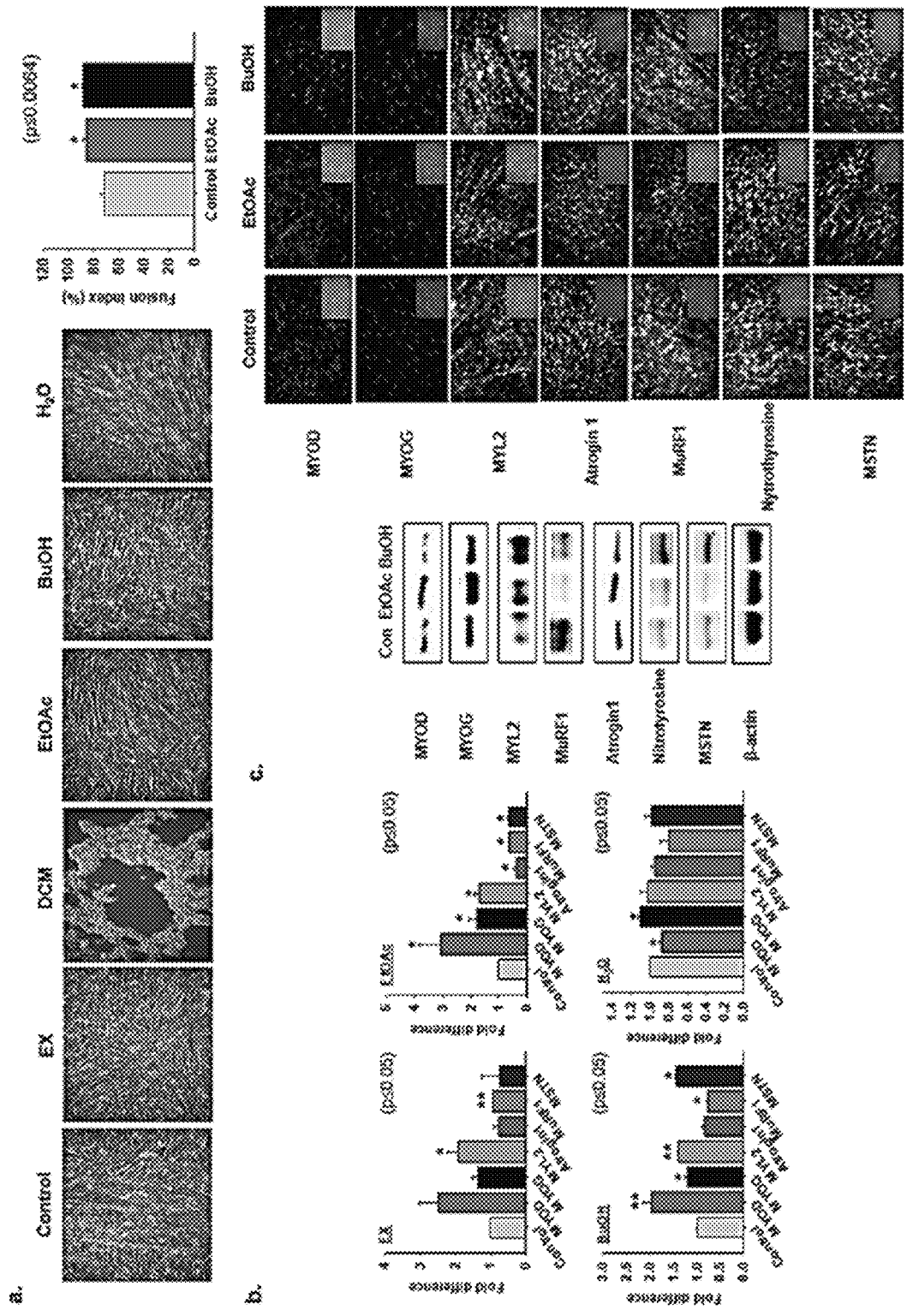
[FIG. 5]

[FIG. 6]
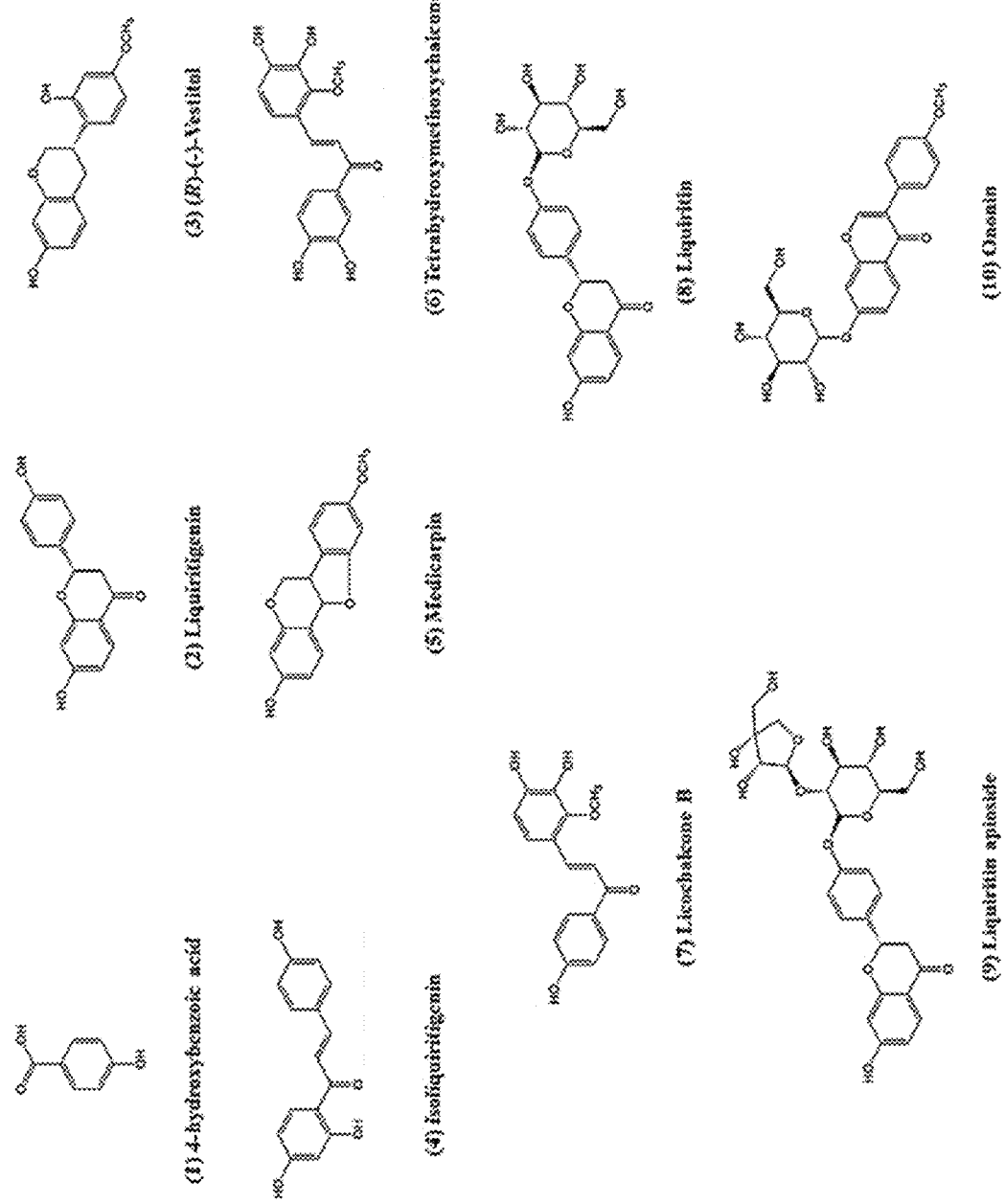

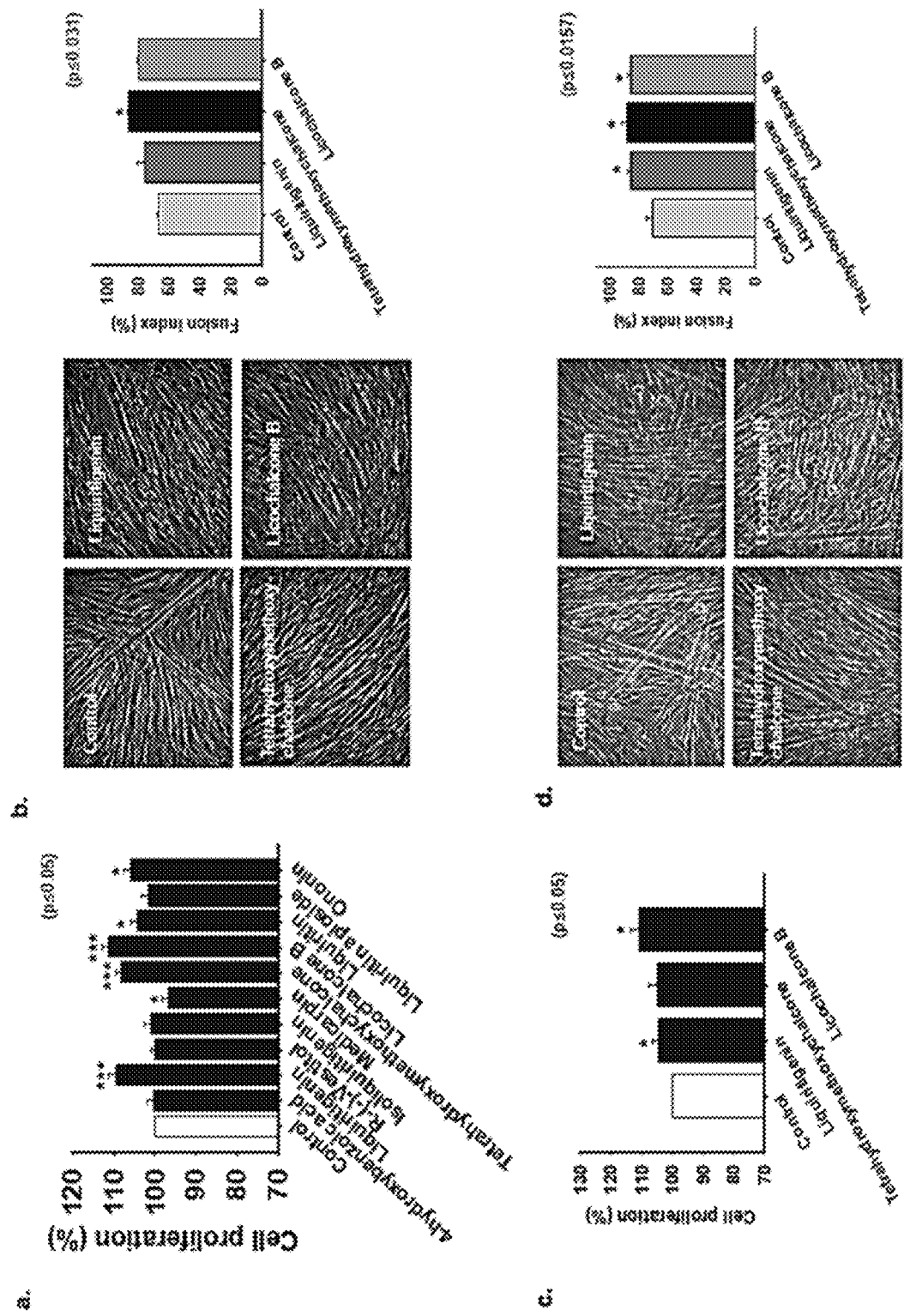
[FIG. 7]

[FIG. 8]
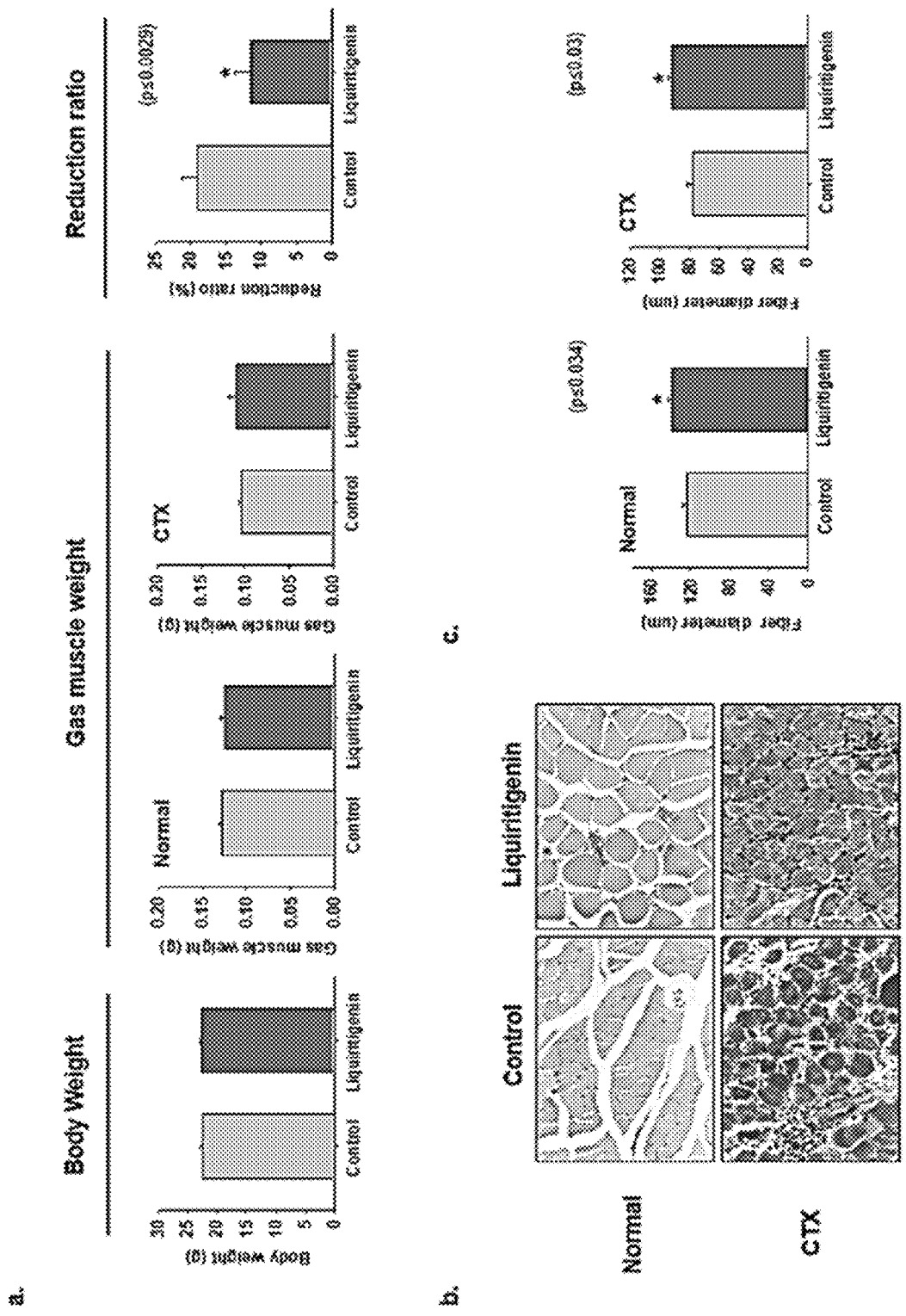

COMPOSITION FOR PREVENTING OR TREATING MUSCULAR DISEASES, CONTAINING, AS ACTIVE INGREDIENT, *GLYCYRRHIZA URALENSIS* EXTRACT OR COMPOUND ISOLATED THEREFROM

CROSS REFERENCE TO PRIOR APPLICATIONS

This application is the 35 U.S.C. 371 national stage of International application PCT/KR2020/007826 filed on Jun. 17, 2020; which claims priority to Korean Patent Application Nos. 10-2019-0072992 filed on Jun. 19, 2019, 10-2020-0073088 filed on Jun. 16, 2020, 10-2020-0073089 filed on Jun. 16, 2020, 10-2020-0073090 filed on Jun. 16, 2020, 10-2020-0073091 filed on Jun. 16, 2020, and 10-2020-0073092 filed on Jun. 16, 2020. The entire contents of each of the above-identified applications are hereby incorporated by reference.

TECHNICAL FIELD

The present invention relates to a composition for preventing or treating muscular diseases, comprising a *Glycyrrhiza uralensis* extract or a compound isolated therefrom as an active ingredient.

BACKGROUND ART

Muscle is an important component consisting of the human body, and is a tissue expressed in stem cells of the mesoderm. Muscles constitute about 40% of our body and are supported by bones and tendons that move together to change the size of cells in order to induce the contraction. Muscles are divided into skeletal muscle, heart muscle, and visceral muscle, and they create physical strength at each location, induce movement, and protect body organs such as bones, joints, and internal organs. In addition, the muscle has a regenerative ability, and when the muscle is damaged, it can be regenerated into a muscle with the original contraction and relaxation ability after being denatured by satellite cells and its surrounding environment.

Muscle diseases are caused by congenital inheritance or environmental causes, and diseases related to muscle loss are increasing with the trend of recent aging society and life span extension. Human muscles decrease by at least 1% every year from the age of 40, and by the age of 80, the level of maximum muscle mass decreases by 50%, and thus, muscle loss in old age is recognized as the most important cause of lowering overall physical function. These muscle diseases are on the rise worldwide compared to the past.

However, since the causes of muscle diseases are more diverse than other diseases, accurate diagnosis is not easy. Based on the severity of symptoms the disease vary according to the type and thus the exact mechanism is rare, as the disease is often not known. The symptoms of muscle disease progress rapidly and muscle disease patients suffer difficulty in their daily life. There are very few fundamental treatments for related diseases.

DISCLOSURE

Technical Problem

It is an object of the present invention to provide a composition for preventing or treating muscle diseases, comprising an extract of a natural substance or compounds isolated therefrom, having an excellent effect for treating muscle diseases as active ingredients.

Technical Solution

In order to achieve the above object, the present invention provides a pharmaceutical composition for preventing or treating muscle diseases comprising licorice extract or a fraction thereof as an active ingredient.

The present invention provides a health functional food composition for preventing or improving muscle diseases comprising licorice extract or a fraction thereof as an active ingredient.

The present invention provides a pharmaceutical composition for preventing or treating muscle diseases comprising a compound represented by any one of Chemical Formulas 1 to 3 or a pharmaceutically acceptable salt thereof as an active ingredient.

[Chemical Formula 1]

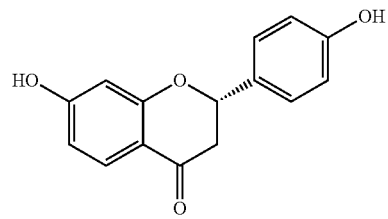

[Chemical Formula 2]

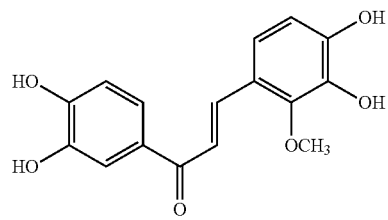

[Chemical Formula 3]

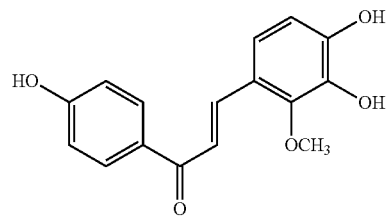

In addition, the present invention provides a health functional food composition for preventing or improving muscle diseases comprising the above compound or a pharmaceutically acceptable salt thereof as an active ingredient.

Advantageous Effects

The licorice extract or a fraction thereof, compounds isolated therefrom, or a pharmaceutically acceptable salt thereof according to the present invention, induce the myoblasts proliferation and promote the differentiation of myoblasts into myotubes. In addition, since it has an excellent effect in regenerating damaged muscles, a pharmaceutical composition or health functional food composition comprising the licorice extract or a fraction thereof, compounds isolated therefrom, or a salt thereof as active ingredients can effectively prevent, ameliorate or treat various muscles diseases.

In addition, the composition has few side effects and is safe by using natural products.

DESCRIPTION OF DRAWINGS

FIG. 1 shows a schematic diagram of a method of preparing a licorice extract or a fraction thereof according to an example of the present invention.

FIG. 2 shows a result of observation of proliferation and differentiation of myoblasts (C2C12) with the treatment of licorice hot water extract; a) is an image and graph confirming the cell proliferation with the concentration of the licorice hot water extract by the MTT assay; b) is an image showing the change with the treatment of licorice hot water extract after applying a scratch to the cell surface; and c) shows results of a fusion index, real-time PCR, Western blot and immunostaining results which confirm the differentiation of myoblasts into myotubes (muscle cell).

FIG. 3 shows a result of analyzing the mouse muscle after the intake of licorice hot water extract; a) is a table showing the body weight and the reduction rate of muscle mass of mouse; b) is a results of Western blot; c) is a graph obtained by specifying and quantifying the intensity of the band from Western blot; and d) is an image showing the change in protein expression through immunostaining.

FIG. 4 shows the result of the proliferation of myoblasts with the treatment of licorice extract fraction; a) is an MTT analysis image and graph of myoblasts; and b) is an image showing the change with the treatment of the fraction after applying a scratch to the cell surface.

FIG. 5 shows the result of observation of myoblasts differentiation with the treatment of licorice extract fraction; a) is a graph showing an image of myotubes formation and fusion index; and b and c) show changes in the expression of muscle differentiation/muscle atrophy genes and proteins with the fraction treatment.

FIG. 6 shows the chemical structure of the final single compounds separated from the ethyl acetate (EtOAc) fraction according to an example of the present invention.

FIG. 7 shows a result of observation of myoblast proliferation and differentiation with the treatment of the final single compounds; a) is a graph showing the change in cell proliferation with the treatment of ten final compounds isolated according to an example of the present invention; b) is images of myotubes formation and a graph showing the fusion index; c) is a graph showing the change in cell proliferation with the treatment of three final compounds purchased; and d) is images of myotubes formation and a graph showing the fusion index.

FIG. 8 shows the result of changes in mouse muscle after the ingestion of liquiritigenin among the purchased final compounds; a) is a graph showing body weight, gastrocnemius muscle weight and muscle mass reductions; b) is a result of H&E staining; and c) is a graph measuring the muscle diameter (μm).

BEST MODE

Hereinafter, the present invention will be described in detail.

The present invention provides a pharmaceutical composition for preventing or treating muscle diseases comprising licorice extract or a fraction thereof as an active ingredient.

The licorice (*Glycyrrhiza uralensis* Fischer) is a medicinal plant belonging to the dicotyledonous rosewood leguminous family and may be obtained by harvesting from nature or cultivating, and may be purchased commercially.

The licorice roots or rhizomes can be used as they are, or can be used by removing the periderm, and preferably, dried roots of licorice can be used.

As used herein, the term "extract" refers to a substance obtained by extracting a component of a natural substance regardless of the extraction method, extraction solvent, extracted component, or form of the extract and it may include all materials that can be obtained by extracting the ingredients of natural substances and followed by processing or treating the extracted materials by other methods.

The licorice extract may be extracted according to a method commonly used in the art, for example, hot water extraction, ultrasonic extraction, filtration, reflux extraction, etc., and these can be performed alone or in combination of two or more methods.

In the present invention, the licorice extract may be extracted with water, C1 to C4 alcohol or a mixed solvent thereof, preferably it may be a hot water extract extracted by heating at 110 to 120° C., more preferably 115° C. for 2 to 4 hours, more preferably 3 hours, with 15 to 25 times, more preferably 20 times distilled water with respect to the weight of the licorice, but it is not limited thereto.

In the present invention, the fraction of the licorice extract may be obtained by fractionating the licorice extract, preferably the hot water extract of the licorice with one or more solvents selected from the group consisting of dichloromethane, ethyl acetate, and n-buthanol, and more preferably, it may be the fraction of the licorice hot water extract fractionated with ethyl acetate.

According to an embodiment of the present invention, after the hot water extract of licorice was suspended in distilled water, dichloromethane, ethyl acetate, and n-butanol were sequentially distributed, and each solution was evaporated to obtain a dichloromethane fraction, an ethyl acetate fraction, and n-butanol fraction.

In the present invention, the licorice extract or a fraction thereof is able to induce the myoblasts proliferation, form a myotube, and promote the differentiation of myoblasts into the muscle cell. In addition, the licorice extract or a fraction thereof inhibits muscle proteolysis and muscle atrophy, and can regenerate the damaged muscles.

The licorice extract or a fraction thereof may increase the expression of one or more genes or proteins selected from the group consisting of MYOG, MYOD, MYL2 and Pax7, which are the myogenic regulatory factors related to muscle differentiation or muscle regeneration, and may reduce the expression of one or more genes or proteins selected from the group consisting of MSTN, MuRF1, Atrogin 1 and nitrotyrosine, which are factors related to muscle proteolysis or muscle atrophy.

MYOD initiates the expression of muscle-specific genes and induces the differentiation of muscle satellite cells into myoblasts. Induction of myogenin (MYOG) expression by the activity of MYOD is the most important factor in the fusion of myoblasts, and is involved in the formation of myotubes, and the muscle fibers formed through this process form a bundle and finally form a muscle.

The present invention provides a pharmaceutical composition for preventing or treating muscle diseases comprising a compound represented by any one of the following Formulas 1 to 3 or a pharmaceutically acceptable salt thereof as an active ingredient.

[Chemical Formula 1]

[Chemical Formula 2]

[Chemical Formula 3]

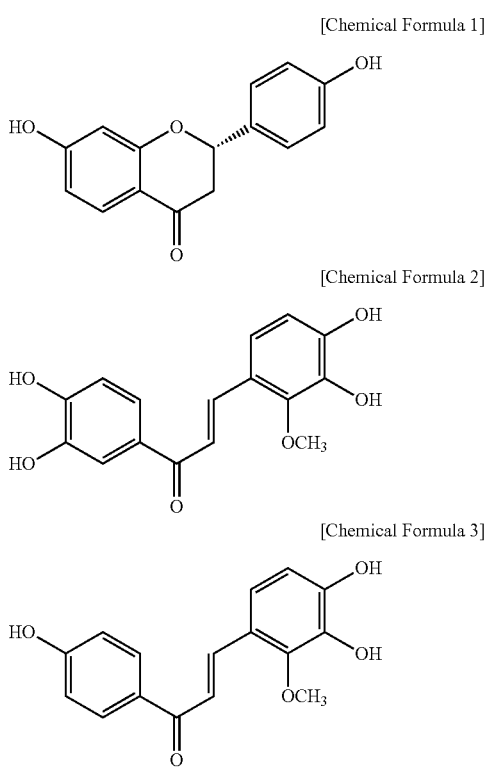

The compounds of Chemical Formulas 1 to 3 are active ingredients isolated from licorice, preferably, Chemical Formula 1 indicate liquiritigenin, Chemical Formula 2 indicate tetrahydroxymethoxychalcone, and Chemical Formula 3 indicate licochalcone B.

The compound or its salt may be directly separated or extracted from natural products by methods well known in the art, or prepared by chemical synthesis, and commercially available ones may be selected and used, but the method or material is not particularly limited.

In the present invention, the compound or a salt thereof may be obtained by separating from the licorice extract extracted with water, C1 to C4 alcohol or a mixed solvent thereof, preferably from a fraction obtained by fractionating the methanol extract of licorice with dichloromethane or ethyl acetate, and preferably, from a fraction obtained by sequentially distributing the methanol extract of licorice with dichloromethane and ethyl acetate, but it is not limited thereto.

More preferably, the compound or a salt thereof may be obtained by suspending the licorice methanol extract obtained by reflux extraction of the dried roots of licorice with 100% methanol, in distilled water, partitioning into dichloromethane, removing dichloromethane from the water fraction thereof, partitioning into ethyl acetate to separate from the ethyl acetate fraction obtained thereby.

More specifically, the compound of Chemical Formula 1 or a salt thereof may be prepared by obtaining 5 fractions (Fr. E1-E5) by silica gel column chromatography of the ethyl acetate fraction with hexane-ethylacetate-methanol (hexane-EtOAc-MeOH, 5.5:1:0.1, 3:1:0.1, v/v), chloroform-acetone-methanol ($CHCl_3$-acetone-MeOH, 3:1:0.1, v/v) and chloroform-methanol-water ($CHCl_3$-MeOH—$H_2O$, 5:1:0.1, 3:1:0.1, v/v), and obtaining 16 fractions (Fr. E2A-E2P) by separating fraction E2 among these by MPLC with a gradient of methanol-water (MeOH-Water, 34-75% MeOH, v/v) using an SNAP Ultra C18 cartridge; and then separating using silica gel column chromatography of fraction E2C among these with a solvent as hexane-ethylacetate-methanol (hexane-EtOAc-MeOH, 3:1:0.1, v/v), but it is not limited thereto.

The compound of Chemical Formula 2 or a salt thereof was prepared by separating the fraction E3 among the five fractions (Fr. E1-E5) separated from the ethyl acetate fraction by MPLC using a SNAP Ultra C18 cartridge with a gradient of methanol-water (MeOH-Water, 33-80% MeOH, v/v) into 15 fractions (Fr. E3A-E3O), and separating fraction E3E among the fractions by MPLC using a SNAP KP-SIL cartridge with a gradient of hexane-ethylacetate-methanol (hexane-EtOAc-MeOH, 28-36% EtOAc-MeOH, 1:0.1, v/v), but it is not limited thereto.

In addition, the compound of Chemical Formula 3 or a salt thereof may be prepared by separating the fraction E3F among the 15 fractions (Fr. E3A-E3O) by MPLC using a SNAP KP-SIL cartridge with a gradient of hexane-ethylacetate-methanol (hexane-EtOAc-MeOH, 20-34% EtOAc-MeOH, 1:0.1, v/v); and separating the fraction E3FB among these by TLC (silica gel 60 F254, hexane-EtOAc-MeOH, 1:1:0.2, v/v), but it is not limited thereto.

The compound can be used in the form of a pharmaceutically or sitologically acceptable salt within a range having the identical efficacy thereto.

As used herein, "pharmaceutically or sitologically acceptable" means that it is not toxic to humans or cells exposed to the composition.

The salt may be used in the form of either a pharmaceutically or sitologically acceptable basic salt or acid salt. The basic salt can be used in the form of an organic base salt or an inorganic base salt, and may be selected from the group consisting of sodium salts, potassium salts, calcium salts, lithium salts, magnesium salts, cesium salts, aluminum salts, ammonium salts, triethylaluminium salts and pyridinium salts.

Acidic salts are useful acid addition salts formed by free acids. Inorganic acids and organic acids can be used as the free acid. Hydrochloric acid, bromic acid, sulfuric acid, sulfurous acid, phosphoric acid, double phosphoric acid, nitric acid, etc. can be used as inorganic acids, and citric acid, acetic acid, maleic acid, fumaric acid, gluconic acid, methanesulfonic acid, benzenesulfonic acid, camphorsulfonic acid, oxalic acid, malonic acid, glutaric acid, acetic acid, glyconic acid, succinic acid, tartaric acid, 4-toluenesulfonic acid, galacturonic acid, embonic acid, glutamic acid, citric acid, aspartic acid, stearic acid, etc. can be used as organic acids, but they are not limited thereto, and all salts formed using various inorganic and organic acids commonly used in the art may be included.

In addition, the compound may include all salts, hydrates, solvates, derivatives, etc. that may be prepared by conventional methods, as well as pharmaceutically or sitologically acceptable salts. The addition salt may be prepared by a conventional method and may be prepared by dissolving in a water-miscible organic solvent, such as acetone, methanol, ethanol, or acetonitrile, adding an excessive amount of organic base or an aqueous base solution of an inorganic base followed by precipitation or crystallization. Alternatively, it may be prepared by evaporating a solvent or an excess base from the mixture and drying to obtain an addition salt, or by suction filtration of the precipitated salt.

In the present invention, the compound or a salt thereof induce the myoblasts proliferation, form a myotube, and promote the differentiation of myoblasts into the muscle cell.

In addition, the compound or a salt thereof inhibit the muscle proteolysis and muscle atrophy, and can regenerate damaged muscles.

In the present invention, the muscle disease is a disease due to a decrease in muscle function, muscle wasting or muscle degeneration, for example, it may be one or more selected from the group consisting of muscle atrophy, muscular dystrophy, sarcopenia, myopathy, myasthenia and muscle injury, but it is not limited thereto.

As used herein, "prevention" means any action of inhibiting the occurrence of or delaying the onset of muscle disease or at least one symptom thereof by administration of the pharmaceutical composition or health functional food composition according to the present invention. In addition, it includes treatment of a subject with remission of the disease to prevent or inhibit recurrence.

As used herein, "treatment" refers to any action that improves or beneficially changes the symptom, such as alleviating, reducing, or eliminating muscle disease or at least one symptom thereof, by administration of the pharmaceutical composition according to the present invention.

As used herein, the "pharmaceutical composition" means a composition administered for a specific purpose. In the present invention, it refers to being administered to prevent or treat muscle disease or at least one symptom thereof.

The pharmaceutical composition according to the present invention can be prepared according to a conventional method in the pharmaceutical field. The pharmaceutical composition may be combined with an appropriate pharmaceutically acceptable carrier according to the formulation, and if necessary, may be prepared by further including excipients, diluents, dispersants, emulsifiers, buffers, stabilizers, binders, disintegrants, solvents, etc. The appropriate carrier does not inhibit the activity and properties of the licorice extract or a fraction thereof according to the present invention, a compound isolated therefrom, or a salt thereof and may be selected depending on the dosage form and formulation.

The pharmaceutical composition according to the present invention may be applied in any formulation form, and more particularly, may be formulated and used in oral formulation or parenteral formulation of external preparations, suppositories and sterile injectable solutions according to conventional methods.

Solid preparations for oral administration include tablets, pills, powders, granules, capsules, and the like, and it may be prepared by mixing at least one excipient, for example, starch, calcium carbonate, sucrose, lactose, sorbitol, mannitol, cellulose, gelatin, etc. and may further include lubricants such as magnesium stearate and talc, in addition to simple excipients. In addition, the capsule formulation may further include a liquid carrier such as fatty oil in addition to the above-mentioned substances.

Liquid preparations for oral administration include suspensions, liquid solutions, emulsions, syrups, and the like and in addition to water and liquid paraffin, which are commonly used simple diluents, various excipients such as wetting agents, sweetening agents, fragrances, preservatives, etc. may be included.

Formulations for parenteral administration include sterile aqueous solutions, non-aqueous solvents, suspending agents, emulsifiers, freeze-drying agents and suppositories. As the non-aqueous solvent and suspending agent, propylene glycol, polyethylene glycol, vegetable oil such as olive oil, injectable ester such as ethyl oleate, and the like may be used. As a base for suppositories, witepsol, macrosol, Tween 61, cacao butter, laurin, glycerogelatin, and the like may be used. It is not limited thereto and any suitable agent known in the art may be used.

In addition, the pharmaceutical composition according to the present invention may further add calcium or vitamins to improve the therapeutic efficacy.

In the present invention, the pharmaceutical composition may be administered in a pharmaceutically effective amount.

As used herein, "a pharmaceutically effective amount" means an amount sufficient to treat a disease at a reasonable benefit/risk ratio applicable to medical treatment and the amount that does not cause side effects.

The effective dosage level of the pharmaceutical composition can be determined differently depending the purpose of use, the patient's age, sex, weight and health condition, the type of disease, the severity, the activity of the drug, the sensitivity to the drug, the method of administration, the administration time, the route of administration and the rate of excretion, the treatment duration, factors including drugs used in combination or concurrently and other factors well known in the medical field. For example, although it is not constant, generally it may be administered in 0.001 to 100 mg/kg and preferably 0.01 to 10 mg/kg once to several times a day. The above dosage does not limit the scope of the present invention in any way.

The pharmaceutical composition according to the present invention may be administered to any animal that may cause muscle disease, and the animal may include, for example, humans and primates as well as livestock such as cattle, pigs, horses, and dogs.

The pharmaceutical composition according to the present invention may be administered by an appropriate route of administration according to the form of the formulation, and may be administered through various routes, such as oral or parenteral, as long as it can reach the target tissue. The method of administration is not particularly limited, and it may be administered by conventional methods such as oral, rectal or intravenous, intramuscular, skin application, inhalation in the respiratory tract, intrauterine septum or intracerebroventricular injection.

The pharmaceutical composition according to the present invention may be used alone for the prevention or treatment of muscle diseases, or may be used in combination with surgery or other drug treatment.

The present invention provides a health functional food composition for preventing or improving muscle diseases comprising licorice extract or a fraction thereof as an active ingredient.

Preferably, the licorice extract may be a licorice hot water extract, and the fraction of the licorice extract may be an ethyl acetate fraction of the licorice hot water extract.

The licorice extract or a fraction induce the myoblasts proliferation and promote the differentiation of myoblasts into myotubes. In addition, the licorice extract or a fraction thereof inhibit muscle proteolysis and muscle atrophy, and regenerate the damaged muscles, and thus can be used as a health functional food composition for preventing or improving muscle diseases.

Corresponding features can be substituted in the above-described section.

The present invention provides the health functional food composition for preventing or improving muscle diseases comprising a compound represented by any one of Chemical Formulas 1 to 3 or a pharmaceutically acceptable salt thereof as an active ingredient.

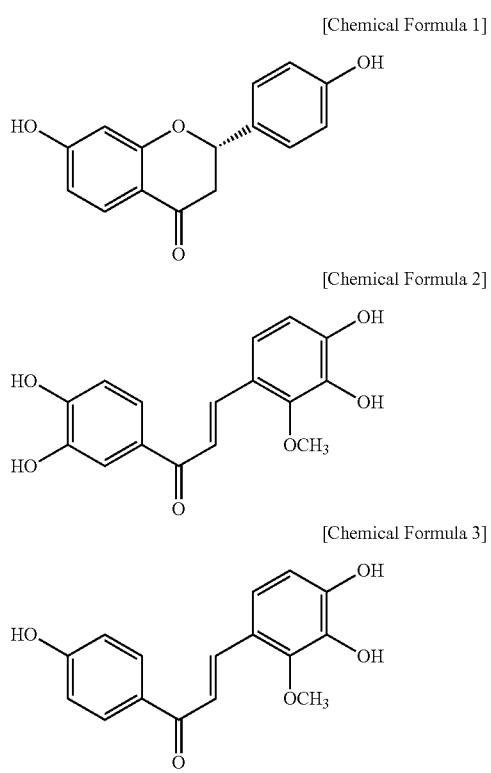

[Chemical Formula 1]

[Chemical Formula 2]

[Chemical Formula 3]

Preferably, the compound or a salt thereof obtained by sequentially distributing the methanol extract of licorice with dichloromethane and ethyl acetate, and may including liquilitigenin, tetrahydroxymethoxychalcone or licochalcone B.

The compound or a salt thereof can proliferate induce myoblasts proliferation and promote differentiation of myoblasts into myotubes. In addition, the compound or a salt thereof inhibit muscle proteolysis and muscle atrophy, and regenerate damaged muscles, and thus can be used as a health functional food composition for preventing or improving muscle diseases.

Corresponding features can be substituted in the above-described section.

As used herein, "improvement" refers to any action that improves or beneficially changes the symptoms such as alleviating, reducing, or eliminating muscle diseases, or at least one symptom thereof, by ingestion of the health functional food composition according to the present invention.

As used herein, "health functional food" includes foods manufactured and processed using raw materials or ingredients having functions useful for the human body according to the Health Functional Food Act No. 6727. The term refers to foods with high medical and medical effects, which processed so that biological control functions such as prevention of muscle diseases, biological defense, immunity and recovery for the purpose of the present invention, in addition to nutrition supply exhibit efficiently.

The health functional food according to the present invention may be prepared as a powder, granule, tablet, capsule, syrup or beverage for the purpose of preventing or improving muscle disease. There is no limitation on the form that the health functional food can be taken, and it can be formulated in the same manner as the pharmaceutical composition and used as a functional food or added to various foods.

The health functional food may include all foods in a conventional sense. For example, it may include beverages and various drinks, fruits and processed foods thereof (canned fruit, jam, etc.), fish, meat and processed foods thereof (ham, bacon, etc.), bread and noodles, cookies and snacks, dairy products (butter, cheese, etc.), and the like, and may include all functional foods in the usual sense. In addition, foods used as feed for animals may also be included.

The health functional food composition according to the present invention may be prepared by further comprising a sitologically acceptable food additive and other appropriate auxiliary ingredients commonly used in the art. The compliance as a food additive is determined by the standards for the applicable item in accordance with General Regulations and General Test Methods of Korean Food Additives Codex approved by the Ministry of Food and Drug Safety, unless otherwise provided. Examples of the items published in the above-mentioned "Korean Food Additives Codex" include chemical synthetics such as ketones, glycine, potassium citrate, nicotinic acid, and cinnamic acid and the like; natural additives such as persimmon color, crystalline cellulose, kaoliang color and guar gum and the like; mixed preparations such as L-sodiumglutamate preparation, alkaline agents for noodles, preservative formulation and a tar color formulation and the like.

The other auxiliary ingredients such as flavoring agents, natural carbohydrates, sweetening agents, vitamins, electrolytes, colorants, pectic acids, alginic acids, organic acids, protective colloidal thickeners, pH adjusters, stabilizers, preservatives, glycerin, alcohols, carbonation agents, etc. may be further included. In particular, as the natural carbohydrate, monosaccharides such as glucose and fructose, disaccharides such as maltose and sucrose, and polysaccharides such as dextrin and cyclodextrin, sugar alcohols such as xylitol, sorbitol, and erythritol may be used. As the sweetener, natural sweeteners such as taumatin and stevia extract, or synthetic sweeteners such as saccharin and aspartame may be used.

The effective dose of the licorice extract or a fraction thereof, a compound isolated therefrom, or a salt thereof contained in the health functional food according to the present invention may be appropriately adjusted according to the purpose of use, such as prevention or improvement of muscle disease.

The health functional food composition has the advantage of not having side effects that may occur when taking general medicines for a long period of time, by using food as a raw material and has excellent portability, and can be ingested as an auxiliary for preventing or improving muscle diseases.

The present invention provides a reagent composition to induce the myoblasts proliferation comprising licorice extract or a fraction thereof as an active ingredient.

The present invention provides a reagent composition to promote the differentiation of myoblasts into myotubes comprising licorice extract or a fraction thereof as an active ingredient.

The present invention provides a reagent composition to induce the myoblasts proliferation comprising a compound represented by any one of the following Chemical Formulas 1 to 3 or a pharmaceutically acceptable salt thereof as an active ingredient.

[Chemical Formula 1]

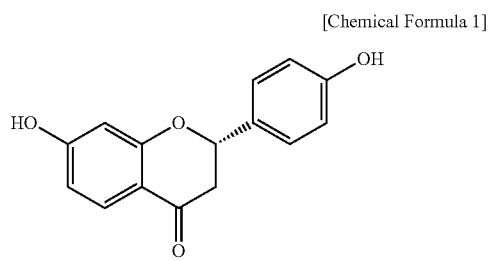

[Chemical Formula 2]

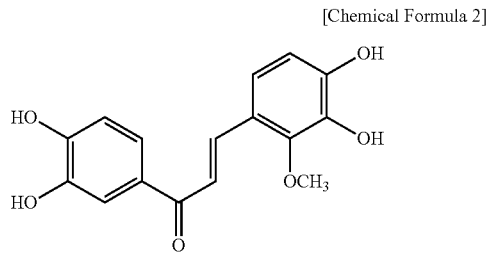

[Chemical Formula 3]

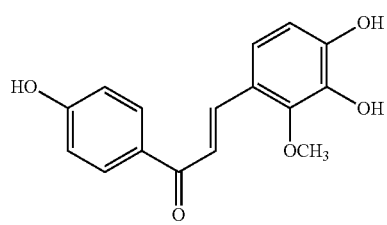

The present invention provides a reagent composition to promote the differentiation of myoblasts into myotubes comprising the compound or a salt thereof as an active ingredient.

In addition, the present invention provides a method of proliferating myoblasts, comprising administering licorice extract or a fraction thereof to animals other than humans.

The present invention provides a method of promoting the differentiation of myoblasts into muscle cells, comprising administering licorice extract or a fraction thereof to animals other than humans.

The present invention provides a method of proliferating myoblasts, comprising administering an animal other than humans with a compound represented by any one of the following Chemical Formulas 1 to 3 or a pharmaceutically acceptable salt thereof.

[Chemical Formula 1]

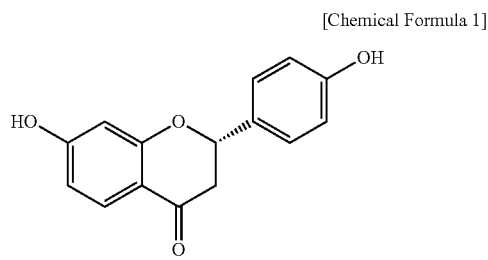

[Chemical Formula 2]

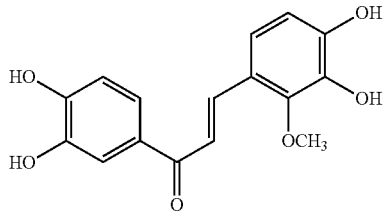

[Chemical Formula 3]

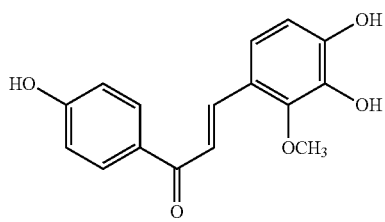

The present invention provides a method of promoting the differentiation of myoblasts into myotube, comprising administering an animal other than humans with the compound or a salt thereof.

Corresponding features can be substituted in the above-described section.

Hereinafter, the present invention has been described in more detail through examples. These examples are only intended to illustrate the present invention in more detail, and it will be apparent to those skilled in the art that the scope of the present invention is not limited by these examples according to the gist of the present invention. The examples of the present invention are provided to more completely explain the present invention to those of ordinary skill in the art.

<Example 1> Preparation of Licorice Extract and Fraction

1. Material Preparation

The dried root of licorice (*Glycyrrhiza uralensis* Fischer) was purchased as a dried herb from Gwangmyeong Herb Store. Specimens of all plants are stored in the Herbal Medicine Bank of the KM Application Center of the Korean Institute of Oriental Medicine.

2. Preparation of Licorice Hot Water Extract

To prepare a licorice hot water extract, dried licorice pieces (50.0 g) were added to 1,000 mL of distilled water and extracted by heating at 115° C. for 3 hours. After extraction, it was filtered and freeze-dried using standard testing sieves (150 μm). The freeze-dried extract powder was dissolved in tertiary distilled water and left at 4° C. for 24 hours. After 24 hours, it was centrifuged at 5000 g for 5 minutes, the supernatant was transferred to a new tube and stored at −20° C.

3. Preparation of Fractions of Licorice Hot Water Extract

FIG. 1 shows a schematic diagram of a method of preparing a licorice extract or a fraction thereof according to an example of the present invention.

As shown in FIG. 1, after suspending the hot water extract of licorice (10.0 g) prepared in step 2 of Example 1 in distilled water, it was partitioned into dichloromethane (DCM, $CH_2Cl_2$), ethyl acetate (EtOAc or EA) and n-butanol (BuOH). Subsequently, each solution was evaporated under reduced pressure at 45° C. to obtain dichloromethane (99.6 mg), ethyl acetate (333.0 mg) and n-butanol (1037.0 mg) fractions, respectively.

4. Final Material Extraction and Separation 4-1. Extraction and Separation Method $^1$H and $^{13}$C NMR spectra were recorded using a BRUKER AVANCE III HD 600 at 600 MHz with tetramethylsilane (TMS) as an internal standard. Medium-pressure liquid chromatography (MPLC) was performed using Isolera One (Biotage, Uppsala, Sweden) equipped with SNAP KP-SIL and SNAP Ultra C18 cartridges. Column chromatography was performed using silica gel (Kieselgel 60, 70-230 and 230-400 mesh, Merck, Darmstadt, Germany), YMC C18 resin, and thin-layer chromatography (TLC) and washed with silica gel 60 F254 and RP-18 F254S plates (0.25 mm, Merck, Darmstadt, Germany), visualized with UV light (254 and 365 nm) and stained with 10% sulfuric acid ($H_2SO_4$).

4-2. Final Material Extraction and Verification

In the same order as in FIG. 1, first, the dried roots of licorice (*Glycyrrhiza uralensis*, 4.2 kg) were extracted with reflux three times with 100% methanol (MeOH) (15 L each). After suspending the methanol extract (957.0 g) in distilled water, it was partitioned with dichloromethane (DCM). After removing the dichloromethane solution from water fraction thereof, it was partitioned with ethyl acetate (EtOAc), and then the ethyl acetate solution was evaporated at 45° C. under reduced pressure to obtain an ethyl acetate fraction (137.0 g).

Silica gel column chromatography of ethyl acetate fraction was performed with hexane-ethylacetate-methanol (hexane-EtOAc-MeOH, 5.5:1:0.1, 3:1:0.1, v/v), and chloroform-acetone-methanol ($CHCl_3$-Acetone-MeOH, 3:1:0.1, v/v), chloroform-methanol-water ($CHCl_3$-MeOH—$H_2O$, 5:1:0.1, 3:1:0.1, v/v) to obtain five fractions (Fr. E1-E5) and semi-crystalline solid (Fr. EC).

Fraction E2 (4.9 g) was separated by a gradient of methanol-water (MeOH-Water, 34-75% MeOH, v/v) by MPLC using a SNAP Ultra C18 cartridge to obtain 16 fractions containing Compound 1 (23.9 mg) (Fr. E2A-E2P).

Compound 1 (4-hydroxybenzoic acid): White powder, $C_7H_6O_3$, $^1$H NMR (600 MHz, MeOD-$d_4$) δ 7.67 (2H, d, J=7.2 Hz, H-2, 6), 6.61 (2H, d, J=7.2 Hz, H-3, 5). $^{13}$C NMR (600 MHz, MeOD-$d_4$) δ 170.1 (C=O), 163.3 (C-4), 132.9 (C-2, 6), 122.7 (C-1), 116.0 (C-3, 5).

Fraction E2C (243.5 mg) was separated using silica gel column chromatography with hexane-ethylacetate-methanol (hexane-EtOAc-MeOH, 3:1:0.1, v/v) solvent to obtain Compound 2 (108.5 mg).

Compound 2 (Liquiritigenin): Colorless needle crystals, $C_{15}H_{12}O_4$, $^1$H NMR (600 MHz, MeOD-$d_4$) δ 7.68 (1H, d, J=8.5 Hz, H-5), 7.28 (2H, d, J=7.6 Hz, H-2', 6'), 6.77 (2H, d, J=7.8 Hz, H-3', 5'), 6.45 (1H, d, J=6.5 Hz, H-6), 6.31 (1H, s, H-8), 5.32 (1H, d, J=12.6 Hz, H-2), 3.00 (1H, t, J=15.0 Hz, H-3a), 2.64 (1H, d, J=16.8 Hz, H-3b). $^{13}$C NMR (600 MHz, MeOD-$d_4$) δ 192.1 (C=O), 165.3 (C-7), 164.1 (C-9), 157.5 (C-4'), 129.9 (C-1'), 128.4 (C-5), 127.6 (C-2', 6'), 114.9 (C-3', 5'), 113.5 (C-10), 110.3 (C-6), 102.4 (C-8), 79.6 (C-2), 43.5 (C-3).

Fraction E2D (420.3 mg) was isolated by MPLC using a SNAP KP-SIL cartridge with a gradient of hexane-ethylacetate-methanol (hexane-EtOAc-MeOH, 17-25% EtOAc-MeOH, 1:0.1, v/v) to obtain Compound 3 (51.7 mg) and Compound 4 (15.4 mg).

Compound 3 ((R)-(−)-Vestitol): Colorless crystals, $C_{16}H_{16}O_4$, $^1$H NMR (600 MHz, Acetone-$d_6$) δ 7.05 (1H, d, J=7.7 Hz, H-6'), 6.89 (1H, d, J=7.1 Hz, H-5), 6.50 (1H, s, H-3'), 6.42 (1H, d, J=6.1 Hz, H-5'), 6.36 (1H, d, J=5.7 Hz, H-6), 6.28 (1H, s, H-8), 4.23 (1H, d, J=6.7 Hz, H-2), 3.98 (1H, t, J=9.5 Hz, H-2), 3.72 (3H, s, —$OCH_3$), 3.47 (1H, m, H-3), 2.99 (1H, m, H-4), 2.82 (1H, d, J=14.8 Hz, H-4). $^{13}$C NMR (600 MHz, Acetone-$d_6$) δ 160.3 (C-4'), 157.4 (C-7), 156.6 (C-2'), 156.1 (C-9), 131.0 (C-5), 128.7 (C-6'), 120.9 (C-1'), 114.3 (C-10), 108.7 (C-6), 105.6 (C-5'), 103.6 (C-8), 102.4 (C-3'), 70.4 (C-2), 55.3 (—OCH3), 32.6 (C-3), 31.0 (C-4).

Compound 4 (Isoliquiritigenin): Yellow crystals, $C_{15}H_{12}O_4$; $^1$H NMR (600 MHz, MeOD-$d_4$) δ 7.90 (1H, d, J=8.2 Hz, H-6'), 7.73 (1H, d, J=15.2 Hz, H-β), 7.56 (3H, s, H-2, 6, α), 6.79 (2H, d, J=8.3 Hz, H-3, 5), 6.36 (1H, dd, J=8.6, 1.6 Hz, H-5'), 6.24 (1H, s, H-3'). $^{13}$C NMR (600 MHz, MeOD-$d_4$) δ 193.5 (C=O), 167.5 (C-4'), 166.3 (C-2'), 161.5 (C-4), 145.6 (C-β), 133.3 (C-6'), 131.8 (C-2, 6), 127.8 (C-1), 118.2 (C-α), 116.9 (C-3, 5), 114.7 (C-1'), 109.1 (C-5'), 103.8 (C-3').

Fraction E2F (95.1 mg) was separated by MPLC using a SNAP KP-SIL cartridge at a gradient of hexane-ethylacetate-methanol (hexane-EtOAc-MeOH, 11-22% EtOAc-MeOH, 1:0.1, v/v) to obtain Compound 5 (11.2 mg).

Compound 5 (Medicarpin): White amorphous powder, $C_{15}H_{14}O_4$, $^1$H NMR (600 MHz, $CDCl_3$) δ 7.39 (1H, d, J=7.5 Hz, H-1), 7.13 (1H, d, J=7.1 Hz, H-7), 6.55 (1H, d, J=6.0 Hz, H-2), 6.45 (2H, s, H-8, -10), 6.42 (1H, s, H-4), 5.50 (1H, d, J=5.8 Hz, H-11a), 4.24 (1H, d, J=5.4 Hz, H-6 eq), 3.77 (3H, s, —$OCH_3$), 3.62 (1H, br t, J=10.4 Hz, H-6ax), 3.54 (1H, d, J=4.3 Hz, H-6a). $^{13}$C NMR (600 MHz, $CDCl_3$) δ 161.2 (C-9), 160.7 (C-10a), 157.1 (C-3), 156.8 (C-4a), 132.3 (C-1), 124.9 (C-7), 119.2 (C-6b), 112.8 (C-11b), 109.9 (C-2), 106.5 (C-8), 103.8 (C-4), 97.0 (C-10), 78.6 (C-11a), 66.6 (C-6), 55.6 (—$OCH_3$), 39.6 (C-6a).

Fraction E3 (41.6 g) was separated by MPLC using a SNAP Ultra C18 cartridge with a gradient of methanol-water (MeOH-Water, 33-80% MeOH, v/v) to obtain 15 fractions (Fr. E3A-E3O). Fraction E3E (140.0 mg) was isolated by MPLC using a SNAP KP-SIL cartridge with a gradient of hexane-ethylacetate-methanol (hexane-EtOAc-MeOH, 28-36% EtOAc-MeOH, 1:0.1, v/v) to obtain Compound 6 (35.2 mg).

Compound 6 (Tetrahydroxy methoxychalcone): Yellow needles, $C_{16}H_{14}O_6$, $^1$H NMR (600 MHz, MeOD-$d_4$) δ 7.89 (1H, d, J=15.6 Hz, H-6), 7.55 (1H, d, J=15.6 Hz, H-α), 7.48 (1H, d, J=6.7 Hz, H-2'), 7.45 (1H, s, H-6'), 7.14 (1H, d, J=7.9 Hz, H-6), 6.82 (1H, d, J=7.5 Hz, H-5'), 6.59 (1H, d, J=7.9 Hz, H-5), 3.78 (3H, s, —$OCH_3$). $^{13}$C NMR (600 MHz, MeOD-$d_4$) δ 191.4 (C=O), 152.1 (C-4'), 150.7 (C-4), 149.9 (C-2), 146.5 (C-3'), 140.9 (C-3), 139.6 (C-β), 131.8 (C-1'), 123.4 (C-6'), 121.4 (C-1), 120.5 (C-α), 120.3 (C-6), 116.3 (C-2'), 115.9 (C-5'), 112.7 (C-5), 61.7 (—$OCH_3$).

Fraction E3F (410.0 mg) was isolated by MPLC using a SNAP KP-SIL cartridge with a gradient of hexane-ethylacetate-methanol (hexane-EtOAc-MeOH, 20-34% EtOAc-MeOH, 1:0.1, v/v) to obtain 5 fractions (Fr. E3FA-E3FE). Fraction E3FB (17.5 mg) was separated by TLC (silica gel 60 F254, hexane-EtOAc-MeOH, 1:1:0.2, v/v) to obtain Compound 7 (5.6 mg).

Compound 7 (Licochalcone B): Yellow needles, $C_{16}H_{14}O_5$, $^1$H NMR (600 MHz, MeOD-$d_4$) δ 7.97-7.91 (3H, m, H-2', 6', β), 7.61 (1H, d, J=15.7 Hz, H-α), 7.19 (1H, d, J=7.9 Hz, H-6), 6.85 (2H, d, J=6.9 Hz, H-3", 5'), 6.61 (1H, d, J=7.5 Hz, H-5), 3.81 (3H, s, —$OCH_3$). $^{13}$C NMR (600 MHz, MeOD-$d_4$) δ 191.3 (C=O), 163.9 (C-4'), 151.0 (C-4), 149.9 (C-2), 141.0 (C-β), 139.7 (C-3), 132.2 (C-2', 6'), 131.1 (C-1'), 121.3 (C-1), 120.4 (C-α), 120.3 (C-6), 116.4 (C-3', 5'), 112.7 (C-5), 61.7 (—OCH$_3$).

Fraction E5 (20.4 g) was isolated by MPLC using a SNAP Ultra C18 cartridge with a gradient of methanol-water (MeOH-Water, 20-44% MeOH, v/v) to obtain 9 fractions (Fr. E5A-E5I). Fraction E5B-D was combined with a gradient of chloroform-methanol-water (CHCl$_3$-MeOH—H$_2$O, 12-20% MeOH—H$_2$O, 1:0.1, v/v) by MPLC using a SNAP KP-SIL cartridge to obtain 5 fractions (Fr. E5BA-E5BE). Fraction E5BA was obtained as a semi-crystalline solid and redistributed in methanol to obtain Compound 8 (969.0 mg).

Compound 8 (Liquiritin): White powder, C$_{21}$H$_{22}$O$_9$, $^1$H NMR (600 MHz, DMSO-d$_6$) δ 7.65 (1H, d, J=7.6 Hz, H-5), 7.44 (2H, s, H-2', 6'), 7.06 (2H, s, H-3', 5'), 6.51 (1H, s, H-6), 6.35 (1H, s, H-8), 4.88 (1H, s, H-1'), 3.68 (1H, s, H-6'), 3.10-3.50 (6H, m, H-2', 3', 4', 5', 6', 3), 2.67 (1H, d, J=15.2 Hz, H-3). $^{13}$C NMR (600 MHz, DMSO-d$_6$) δ 190.4 (C=O), 165.1 (C-7), 163.5 (C-9), 157.9 (C-4'), 132.8 (C-1'), 128.8 (C-5), 128.4 (C-2', 6'), 116.6 (C-3', 5'), 114.0 (C-10), 111.0 (C-6), 103.0 (C-8), 100.7 (C-1'), 79.1 (C-2), 77.5 (C-5'), 77.0 (C-3'), 73.6 (C-2'), 70.1 (C-4'), 61.1 (C-6'), 43.6 (C-3).

Fraction ESBB-C was combined and separated using silica gel column chromatography with a chloroform-methanol-water (CHCl$_3$-MeOH—H$_2$O, 7:1:0.05, 6:1:0.05 and MeOH, v/v) solvent to obtain 6 fractions (Fr. E5BBA-E5BBF). Fraction E5BBD (220.0 mg) was isolated by MPLC using a SNAP KP-SIL cartridge at a gradient of ethyl acetate-methanol-water (EtOAc-MeOH—H$_2$O, 4-10% MeOH—H$_2$O, 1:0.1, v/v) to obtain Compound 9 (113.5 mg).

Compound 9 (Liquiritin apioside): Yellow powder, C$_{26}$H$_{30}$O$_{13}$, $^1$H NMR (600 MHz, MeOD-d$_4$) δ 7.71 (1H, d, J=8.3 Hz, H-5), 7.41 (2H, d, J=6.9 Hz, H-2', 6'), 7.09 (2H, s, H-3', 5'), 6.48 (1H, d, J=6.4 Hz, H-6), 6.34 (1H, s, H-8), 5.44 (1H, br s, H-1'), 5.40 (1H, s, H-2), 4.98 (1H, d, J=7.0 Hz, H-1'), 3.01 (1H, t, J=14.5 Hz, H-3), 2.70 (1H, t, J=16.8 Hz, H-3). $^{13}$C NMR (600 MHz, MeOD-d$_4$) 193.2 (C=O), 166.8 (C-7), 165.4 (C-9), 159.1 (C-4'), 134.3 (C-1'), 129.8 (C-5), 128.8 (C-2', 6'), 117.5 (C-3', 5'), 115.0 (C-10), 111.8 (C-6), 110.7 (0-1'), 103.8 (C-8), 100.7 (C-1'), 80.7 (C-3'), 80.7 (C-2), 78.6 (C-2'), 78.5 (C-3'), 78.0 (C-2'), 78.0 (C-5'), 75.4 (C-4'), 71.3 (C-4'), 66.0 (C-5'), 62.4 (C-6'), 44.9 (C-3).

Fraction EC (3.0 g) was separated by MPLC using SNAP KP-SIL cartridge with a gradient of chloroform-methanol-water (CHCl$_3$-MeOH—H$_2$O, 12-16% MeOH—H$_2$O, 1:0.1, 100% Acetone, v/v) to obtain 1 fraction and re-dispersed in methanol to obtain Compound 10 (22.2 mg).

Compound 10 (Ononin): White powder, C$_{22}$H$_{22}$O$_9$, $^1$H NMR (600 MHz, DMSO-d$_6$) δ 8.43 (1H, s, H-2), 8.05 (1H, d, J=8.5 Hz, H-5), 7.53 (2H, d, J=7.5 Hz, H-2', 6'), 7.24 (1H, s, H-8), 7.15 (1H, d, J=8.1 Hz, H-6), 6.99 (2H, d, J=7.6 Hz, H-3', 5'), 5.12 (1H, d, J=7.8 Hz, H-1'), 3.78 (3H, s, —OCH$_3$), 3.73 (1H, m, C-6'), 3.19-3.48 (5H, m, H-2', 3', 4', 5', 6'). $^{13}$C NMR (600 MHz, DMSO-d$_6$) δ 175.1 (C-4), 161.9 (C-7), 159.4 (C-4'), 157.5 (C-9), 154.1 (C-2), 130.5 (C-2", 6'), 127.4 (C-5), 124.4 (C-1'), 123.8 (C-3), 118.9 (C-10), 116.0 (C-6), 114.0 (C-3", 5'), 103.8 (C-8), 100.4 (C-1'), 77.6 (C-5'), 76.9 (C-3'), 735. (C-2'), 70.7 (C-4'), 61.0 (C-6'), 55.6 (—OCH$_3$).

<Experimental Example 1> Confirmation of Effects on Myoblasts Proliferation, Differentiation and Muscle Regeneration with Treatment of Licorice Extract or Fractions Thereof Treatment 1. Experimental Method 1-1. C2C12 Cell Culture and Observation of Proliferation with Treatment of Licorice Hot Water Extract, Fraction Thereof or Final Compounds C2C12 cells, a mouse myoblast cell line, were cultured in Dulbecco's Modified Eagle's Medium (DMEM) containing 10% Fetal bovine serum (FBS) and 1% Penicillin/streptomycin (P/S).

To verify the effect of the hot water extract of licorice, its fraction or the final material, C2C12 cells (2×10$^3$ cells/ml) were placed in a 12 well cell culture dish and adhered for 24 hours, followed by treatment of hot water extract (0, 50, 100, 200 μg/ml), a fraction thereof (25 μg/ml) or a final compounds (0.5 ng/ml) for 1 day to confirm the proliferation of cells. The medium was changed every 2 days and the cells were cultured at 37° C.

1-2. Scratch Experiment

When the C2C12 cells reached at 100% confluency, a scratch was applied to the cell surface and hot water extract (50 μg/ml) or a fraction thereof (25 μg/ml) was treated and cultured for 1 day, and the degree of recovery of the cells was observed by microscope.

1-3. Myoblast Proliferation Verification (MTT Assay)

To verify cell proliferation, the cell culture medium was removed and the cells was washed with DMEM, and then 500 μl of MTT reagent (0.5 mg/ml) dissolved in phosphate buffered saline (PBS) was added to each well and left for 1 hour at 37° C. The reaction solution was removed and 1000 μl of dimethyl sulfoxide (DMSO) was added to each well. Purple formazan crystals were completely dissolved in DMSO and absorbance was measured at 540 nm.

1-4. Differentiation Observation with Licorice Hot Water Extract, its Fraction and Final Material Treatment To induce the differentiation, when cells grow at least about 70%, proliferation media was switched to differentiation media [DMEM+2% FBS+1% P/S], supplemented with the hot water extract (100 μg/ml), fraction (25 μg/ml) or final material (0.25 ng/ml) and then incubated for 2 or 4 days. The medium was changed every 2 days and the cells were cultured at 37° C.

1-5. Giemsa Stain and Fusion Index

The medium of the cells was removed and the cells were washed with PBS. After washing, a 1:1 volume ratio of methanol:PBS was treated and then fixed for 2 minutes. Additionally, a 2:1 volume ratio of methanol:PBS reagent was added, followed by further fixation for 2 minutes. After 2 minutes, 0.04% Giemsa reagent was added, allowed to stand for 30 minutes, washed with PBS after 30 minutes, and then the appearance of the cells was observed under a microscope, and three photos of the cells were taken (300×). In the photographs taken, the number of fused nuclei in the myotube cells was counted, the total number of nuclei was counted, and the number of fused nuclei was divided by the total number of nuclei to calculate % value.

1-6. RNA Extraction and cDNA Synthesis

After adding 1 ml of a TRIzol™ reagent, the cells were crushed using an ultrahigh frequency sonicator. After centrifuging the pulverized sample (12,000 rpm, 10 minutes, 4° C.), the supernatant was transferred to a new tube, 200 μl of chloroform was added and left at room temperature for 10 minutes. Then, centrifugation was performed (12,000 rpm, 10 minutes, 4° C.) to obtain a transparent supernatant.

Next, 500 μl of isopropanol was added, allowed to stand for 10 minutes and centrifuged to obtain a RNA pellet. The RNA was washed by adding 70% ethanol (ethanol+diethylpyrocarbonate (DEPC) treated distilled water) and was completely removed and dried. DEPC-treated distilled water was added to the dried transparent RNA and stored at −80° C. The total amount of RNA was measured by nanodrops, and 18s and 28s bands were identified on a 1.2% agarose gel. A cDNA was synthesized with 2 μg of total RNA, random hexamer primer, and reverse transcriptase (25° C.: 10 minutes, 37° C.: 120 minutes, 85° C.: 5 minutes).

1-7. Gene Expression Verification

Real-time PCR was performed to confirm gene expression. The gene expression was analyzed using the Power SYBR Green PCR Master Mix containing a fluorescent material of SYBR green to observe the real-time gene expression (7500 real-time PCR system). PCR primers were designed with Primer 3 software (http://frodo.wi.mit.edu) as per the nucleotide sequence obtained from NCBI GenBank.

PCR was carried out 40 times at 95° C. for 10 minutes, again at 95° C. for 33 seconds, 33 seconds at the gene primer temperature (tm), and 33 seconds at 72° C. Gene expression values were analyzed through analysis of c(t) values obtained through real-time PCR analysis (fold change $2^{-\Delta\Delta Ct}$ formula). The gene expression value of the treated cells was calculated by setting the gene expression value of the untreated cell as 1. When analyzing the gene c(t) value, the GAPDH (Glyceraldehyde-3-phosphate dehydrogenase) gene was used for normalization.

The sequence of the PCR primers is shown in Table 1 below.

1-9. Western Blot

The medium of the cultured C2C12 cells was removed and washed with PBS. After adding RIPA buffer (Radioimmunoprecipitation assay buffer, Thermo) and a protease inhibitor (Thermo) to the washed cells, the cells were lysed to extract the proteins. The extracted proteins of 40 μg was electrophoresed on an 8 to 10% acrylamide gel, and then transferred to a PVDF membrane (Polyvinylidene fluoride membrane, Milipore). It was blocked with 3% skim milk or bovine serum albumin (BSA) for 1 hour at room temperature. Thereafter, the primary antibody diluted in 1% skim milk or BSA (MYOD: 1:500, MYOG: 1:400, MYL2: 1:1000, ß-actin: 1:1000, MuRF1: 1:500, Atrogin 1: 1:500, Nitrotyrosine: 1:10000, MSTN: 1:500, GAPDH: 1:1000) was added and reacted at 4° C. for 16 hours or longer. After 16 hours, it was washed three times with TBST (Tween 20-containing Tris-Buffered Saline) and incubated with horse radish peroxidase (HRP)-conjugated secondary antibody for 1 hour at room temperature. It was washed 3 times with TBST and developed with adding Super Signal West Pico Chemiluminescent Substrate.

1-10. Immunohistochemistry

Paraffin embedded tissue sections were deparaffinized, hydrated, and endogenous peroxidase was quenched using xylene, an ethanol gradient, and methanol/$H_2O_2$, respectively. After blocking with 1% normal goat serum, sections were incubated with primary antibody (1:50) over 16 hours

TABLE 1

| Gene | Product size(bp) | Tm (° C.) | Sequence (F) | Sequence (R) |
|---|---|---|---|---|
| GAPDH | 155 | 59 | 5'-tgctggtgctgagtatgtcg-3' (SEQ ID NO: 1) | 5'-caagcagttggtggtacagg-3' (SEQ ID NO: 2) |
| MYOD | 213 | 59 | 5'-aggagcacgcacacttctct-3' (SEQ ID NO: 3) | 5-tctcgaaggcctcattcact-3' (SEQ ID NO: 4) |
| MYOG | 185 | 59 | 5-tccagtacattgagcgccta-3' (SEQ ID NO: 5) | 5'-caaatgatctcctgggttgg-3' (SEQ ID NO: 6) |
| MYL2 | 177 | 59 | 5'-aaagaggctccaggtccaat-3' (SEQ ID NO: 7) | 5'-cctctctgcttgtgtggtca-3' (SEQ ID NO: 8) |
| Atrogin1 | 160 | 59 | 5'-ttcagcagcctgaactacga-3' (SEQ ID NO: 9) | 5'-tgaaagcttcccccaaagta-3' (SEQ ID NO: 10) |
| MuRf1 | 206 | 59 | 5'-tgaggtgcctacttgctcct-3' (SEQ ID NO: 11) | 5'-tcacctggtggctattctcc-3' (SEQ ID NO: 12) |
| MSTN | 163 | 59 | 5'-acgctaccacggaaacaatc-3' (SEQ ID NO: 13) | 5'-ggagtcttgacgggtctgag-3' (SEQ ID NO: 14) |

1-8. Cell Tissue Immunocytochemistry

The medium of the cultured C2C12 cells was removed and washed once with PBS. Cells were fixed with 4% formaldehyde for 15 min and washed with PBS and 0.2% trypton X-100 (Sigma) was added and leave for 5 minutes. It was washed again with PBS, enhancer solution was added and leave for 30 minutes and then primary antibodies (MYOD, MYOG, Myosin light chain 2 (MYL2), Atrogin 1, MuRF1, Nitrothyrosine, MSTN, 1:50) was added and reacted at 4° C. for 14 hours. The antibody was removed, washed 3 times with PBS for 10 minutes, and incubated with a secondary antibody (Alexa Fluor 488 goat anti-rabbit or mouse SFX kit) for 1 hour. After incubation, the antibody at 4° C. After 16 hours, it was washed three times in PBS, and then treated with HRP-conjugated secondary antibody (1:100) at room temperature for 1 h. Sections were then counterstained with hematoxylin, dehydrated, mounted, and examined under a light microscope. Horse radish peroxidase-conjugated streptavidin was added to detect protein expression and was observed through a microscope.

1-11. Observation of Muscle Regeneration Effect with the Licorice Hot Water Extract Diet In order to observe the muscle regeneration effect according to the treatment of hot water extract of licorice or the final substance liquiritigenin, the mice were ingested with licorice hot water extract or liquiritigenin and Cardiotoxin (CTX) was/was not injected into the muscle and then the morphology and regeneration of the muscles were observed. C57BL/6 mice were ingested with licorice hot water extract (100 mg/kg) or liquiritigenin (15 mg/kg) and 100 mM cardiotoxin was injected into the gastrocnemius muscle. After cardiotoxin injection, licorice hot water extract or liquiritigenin was ingested every day, and muscle tissue was sampled 7 days after non-injection or injection of cardiotoxin. The diameter (μm) of the muscle secured 7 days after non-injection or injection of cardiotoxin was measured using an image J program.

2. Experiment Result 2-1. Proliferation and Differentiation of Myoblasts with the Licorice Hot Water Extract Treatment In order to examine the proliferation of myoblasts with the licorice hot water extract treatment, C2C12 cells were treated with 0, 50, 100, 200 μg/ml of the hot water extract for 1 day and then cell proliferation was analyzed by the MTT method.

FIG. 2 shows the result of proliferation and differentiation of myoblasts (C2C12) with the licorice hot water extract treatment, where for the degree of myoblasts proliferation, the relative value of cells treated with the licorice hot water extract was calculated by setting the value of the cells to which nothing was treated as 100, and for the degree of differentiation and gene expression, the relative value of the cells treated with the licorice hot water extract was calculated by setting the value of the cells to which nothing was treated as 1. The same applies in the following experiments.

Referring to FIG. 2a, when the cells were treated with 50 and 100 μg/ml of licorice hot water extract, it was confirmed that cells were proliferated by about 20% compared to cells not treated with the extract. In addition, as shown in FIG. 2b, when 50 μg/ml of licorice hot water extract was treated for 1 day after applying a scratch to C2C12 cells, it was found that the degree of recovery of cells treated with the extract was higher than that of cells not treated with the extract.

Referring to FIG. 2c, in order to examine the differentiation of C2C12 cells with the treatment of licorice hot water extract, the cells were treated with 2% FBS differentiation medium together with the licorice hot water extract (100 μg/ml) and cultured for 4 days and as a result, myotube formation was observed in the cells treated with the extract, and the expression of genes or proteins such as MYOD, MYOG, and MYL2 are increased in differentiated cells. In addition, it was found that the expression of Atrogin 1, MuRF1 genes or proteins related to proteolysis and muscle atrophy was decreased.

2-2. Muscle Regeneration Effect by Treatment of Licorice Hot Water Extract

In order to study the muscle regeneration effect of the licorice hot water extract treatment, after ingesting the licorice hot water extract into the mouse, CTX was injected into the mouse muscle to analyze the degree of regeneration of the damaged muscle. In addition, in order to verify the effect of the extract even in intact muscles, the expression of related proteins was observed after feeding the licorice hot water extract.

FIG. 3 shows the result of mouse muscle with the intake of the licorice hot water extract. Referring to the figure a, there was little change in body weight between the mice ingesting the licorice hot water extract and the mice not ingesting, but it was found that the reduction ratio of muscle of the mice ingesting the extract was less than that of the mice not ingesting.

Referring to FIGS. 3 b, c and d, the expression of proteins Pax7, MYOD, MYOG and MYL2, which are highly expressed during muscle regeneration in the muscles of mice injected with licorice hot water extract/CTX, was increased compared to the mice injected with CTX alone. The expression of MSTN, MuRF1, Atrogin 1 and Nitrotyrosine proteins related to muscle differentiation inhibition, proteolysis and muscle atrophy in the muscles of mice injected with licorice hot water extract/CTX was decreased compared to mice injected with CTX alone. However, in the muscle of the mouse that did not damage the muscle, the difference in protein expression with the intake of licorice hot water extract could not be observed.

2-3. Proliferation of Myoblasts by Treatment of Licorice Extract Fraction

In order to examine the proliferation of myoblasts with the treatment of the licorice extract fraction, C2C12 cells were treated with 5 fractions (25 μg/ml) for 1 day and then the proliferation of cells was analyzed by the MTT method.

FIG. 4 shows the results of myoblast proliferation with the treatment of the licorice extract fraction. Cells treated with the ethyl acetate fraction of licorice (EtOAc, 12%) or with the n-butanol fraction (BuOH, 12%), as well as the cells treated with the licorice hot water extract (EX, 10%) showed an increase in cell proliferation compared to cells not treated with the extract or the fraction. However, the cells treated with the dichloromethane (DCM) fraction showed a decrease in cell proliferation compared to the untreated cells (27%).

In addition, as a result of incubating for 1 day by applying a scratch to the cells followed by treating the fractions, it was found that the cells treated with the ethyl acetate fraction had higher recovery at the scratched area of the cells compared to the untreated cells.

2-4. Differentiation of Myoblasts by Treatment of Licorice Extract Fraction

In order to confirm the differentiation of C2C12 cells with the treatment of the licorice extract fraction, the cells were treated with 2% FBS differentiation medium, and with the fractions (25 μg/ml), and cultured for 4 days.

FIG. 5 shows the result of differentiation of myoblasts with the treatment of the fraction of licorice extract. it was found that the myotube formation was increased with the treatment of the ethyl acetate (EtOAc) fraction of licorice. Furthermore, it was confirmed that the expression of MYOD, MYOG, and MYL2 genes and proteins related to the muscle differentiation was increased, and the expression of Atrogin 1, MuRF1 and MSTN genes related to the protein degradation, muscle atrophy, and differentiation inhibition was decreased. In addition, it was found that the expression of MuRF1 and MSTN proteins was decreased.

Even when the n-butanol (BuOH) fraction of licorice was treated, it was found that myotube formation was increased, and the expression of MYOG and MYL2 genes and proteins increased and the expression of Atrogin 1 and MuRF1 genes decreased. Even when the licorice hot water extract (EX) was treated the expression of MYL2 gene increased and the expression of Atrogin 1 and MuRF1 genes decreased, and when the water ($H_2O$) fraction was treated the expression of MYOG gene slightly increased but the expression of other related genes did not show any change.

2-5. Cell Proliferation with the Final Single Compound Treatment

FIG. 6 shows the chemical structure of single compound separated from an ethyl acetate (EtOAc) fraction. according to an example of the present invention. After separating 10 final compounds from the fractions through several stages of fractionation, structural analysis was performed.

Table 2 shows the separated 10 final compounds and analysis results thereof.

TABLE 2

| Name | Weight (mg) | NMR sample | | |
|---|---|---|---|---|
| | | Weight (mg) | Solvent | Spectra |
| 4-hydroxybenzoic acid | 23.9 | 23.9 | MeOD | 600 MHz, 1H, 13C |
| Liquiritigenin | 108.5 | 14.5 | MeOD | 600 MHz, 1H, 13C |
| R-(−)-Vestitol | 51.7 | 15.4 | MeOD | 600 MHz, 1H, 13C |
| Isoliquiritigenin | 145.5 | 14.7 | MeOD | 600 MHz, 1H, 13C |
| Medicarpin | 11.2 | 9.70 | MeOD | 600 MHz, 1H, 13C |
| Tetrahydroxymethoxychalcone | 35.2 | 31.0 | MeOD | 600 MHz, 1H, 13C |
| Licochalcone B | 5.6 | 5.0 | MeOD | 600 MHz, 1H, 13C |
| Liquiritin | 969 | 15.7 | DMSO-D6 | 600 MHz, 1H, 13C |
| Liquiritin apioside | 113.5 | 14.0 | MeOD | 600 MHz, 1H, 13C |
| Ononin | 22.2 | 20 | DMSO-D6 | 600 MHz, 1H, 13C |

In order to observe the proliferation of C2C12 cells with the treatment of final compounds, 0.5 ng/ml of final compounds were treated for 1 day and the proliferation of the cells was observed by the MTT method.

FIG. 7 shows the result of myoblast proliferation and differentiation with the treatment of the final single compound. Referring to FIG. 7a, cells treated with 0.5 ng/ml of liquiritigenin (10%), tetrahydroxymethoxychalcone (8%) or licochalcone B (11%) showed increased proliferation of cells compared to cells not treated with the compound.

Referring to FIG. 7b, it was found that myotube formation and fusion index increased with treatment with liquiritigenin (13%), tetrahydroxy methoxychalcone (28%) or licochalcone B (19%). Referring FIG. 7c, it was found that the proliferation of cells treated with purchased liquiritigenin (0.25 ng/ml, 5%), tetrahydroxy methoxychalcone (0.25 ng/ml, 5%) or licochalcone B (1 ng/ml, 11%) was increased compared to the non-treated cells. In addition, referring FIG. 7d, it was found that the myotube formation and fusion index increased with treatment with liquiritigenin (20%), tetrahydroxy methoxychalcone (23%) or licochalcone B (20%).

2-6. Muscle Regeneration Effect with Liquiritigenin Treatment

In order to check the muscle regeneration effect with liquiritigenin treatment, the degree of regeneration of the damaged muscle was observed by measuring the diameter of the regenerated muscle after ingesting liquiritigenin into the mouse and then injecting CTX into the mouse muscle.

FIG. 8 shows the changes in muscle after ingesting purchased liquiritigenin into a mouse. Body and gastrocnemius muscle weights were similar for liquiritigenin treated and non-treated controls at 8a. However, muscle mass reductions in liquiritigenin treated mice were less than in non-treated controls.

Referring to FIGS. 8b and c, the diameter of the regenerated muscle of the mice ingesting liquiritigenin was wider compared to that of the mice not ingested (the muscle diameter of the mouse not ingested: 78±4 µm, the muscle diameter of the mouse ingested: 91±3 µm). The muscle fiber size is increased after liquiritigenin treatment, both in non-injected and in CTX-injected regenerating muscles compared to non-treated ones (the muscle diameter of the mouse not ingested: 124±4 µm, the muscle diameter of the mouse ingested: 139±4 µm).

While the present invention has been particularly described with reference to specific embodiments thereof, it is apparent that this specific description is only a preferred embodiment and that the scope of the present invention is not limited thereby to those skilled in the art. That is, the practical scope of the present invention is defined by the appended claims and their equivalents.

The invention claimed is:

1. A method of preventing or treating muscle diseases in a subject, comprising:

provinding a pharmaceutical composition comprising licorice extract containing a compound represented by the following formula 3, as an active ingredient,

[Chemical Formula 3]

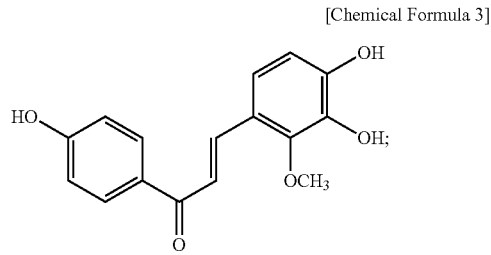 [SMILES: COc1c(/C=C/C(=O)c2ccc(O)cc2)ccc(O)c1O]

and administering the pharmaceutical composition to the subject, wherein the muscle diseases are prevented or treated, wherein the muscle diseases are selected from the group consisting of muscular dystrophy, sarcopenia, myopathy, and myasthenia, wherein the compound is obtained by extracting licorice with distilled water at 110 to 120° C. for 2 to 4 hours and fractioning the licorice extract with dichloromethane ethyl acetate or N-butanol.

2. The method of claim 1, wherein the licorice extract or a fraction thereof proliferates myoblasts, forms myotubes and promotes differentiation into muscle cells.

3. The method of claim 1, wherein the licorice extract or a fraction thereof regenerates damaged muscles.

4. The method of claim 1, wherein the licorice extract or a fraction thereof inhibits muscle proteolysis.

5. The method of claim 1, wherein the licorice extract or a fraction thereof increases expression of at least one muscle differentiation-related factors selected from the group consisting of MYOG, MYOD, MYL2 and Pax7, and reduces expression of at least one muscle proteolysis-related factors selected from the group consisting of MSTN, MuRF1, Atrogin 1 and nitrotyrosine.

6. A method of preventing or improving muscle diseases in a subject, comprising:

providing a health functional food composition comprising licorice extract containing a compound represented by the following formula 3, as an active ingredient,

[Chemical Formula 3]

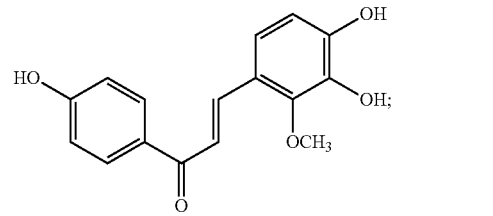

and administering the health functional food composition to the subject, wherein the muscle diseases are prevented or improved, wherein the muscle diseases are selected from the group consisting of muscular dystrophy, sarcopenia, myopathy, and myasthenia, wherein the compound is obtained by extracting licorice with distilled water at 110 to 120° C. for 2 to 4 hours and fractioning the licorice extract with dichloromethane, ethyl acetate or N-butanol.

7. The method of claim 1, wherein the licorice extract contains a compound represented by Chemical Formula 2,

[Chemical Formula 2]

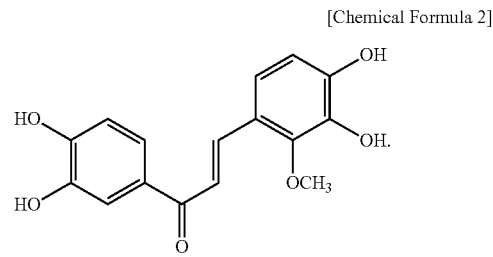 [SMILES: COc1c(/C=C/C(=O)c2ccc(O)c(O)c2)ccc(O)c1O]

* * * * *

SEQUENCE LISTING

<160> NUMBER OF SEQ ID NOS: 14

<210> SEQ ID NO 1
<211> LENGTH: 20
<212> TYPE: DNA
<213> ORGANISM: Artificial Sequence
<220> FEATURE:
<223> OTHER INFORMATION: GAPDH-f

<400> SEQUENCE: 1
tgctggtgct gagtatgtcg            20

<210> SEQ ID NO 2
<211> LENGTH: 20
<212> TYPE: DNA
<213> ORGANISM: Artificial Sequence
<220> FEATURE:
<223> OTHER INFORMATION: GAPDH-r

<400> SEQUENCE: 2
caagcagttg gtggtacagg            20

<210> SEQ ID NO 3
<211> LENGTH: 20
<212> TYPE: DNA
<213> ORGANISM: Artificial Sequence
<220> FEATURE:
<223> OTHER INFORMATION: MYOD-f

<400> SEQUENCE: 3
aggagcacgc acacttctct            20

<210> SEQ ID NO 4
<211> LENGTH: 20
<212> TYPE: DNA
<213> ORGANISM: Artificial Sequence
<220> FEATURE:
<223> OTHER INFORMATION: MYOD-r

<400> SEQUENCE: 4
tctcgaaggc ctcattcact            20

<210> SEQ ID NO 5
<211> LENGTH: 20
<212> TYPE: DNA
<213> ORGANISM: Artificial Sequence
<220> FEATURE:
<223> OTHER INFORMATION: MYOG-f

<400> SEQUENCE: 5
tccagtacat tgagcgccta            20

<210> SEQ ID NO 6
<211> LENGTH: 20
<212> TYPE: DNA
<213> ORGANISM: Artificial Sequence
<220> FEATURE:
<223> OTHER INFORMATION: MYOG-r

<400> SEQUENCE: 6
caaatgatct cctgggttgg            20

<210> SEQ ID NO 7
<211> LENGTH: 20
<212> TYPE: DNA
<213> ORGANISM: Artificial Sequence

```
<220> FEATURE:
<223> OTHER INFORMATION: MYL2-f

<400> SEQUENCE: 7
aaagaggctc caggtccaat                                                  20

<210> SEQ ID NO 8
<211> LENGTH: 20
<212> TYPE: DNA
<213> ORGANISM: Artificial Sequence
<220> FEATURE:
<223> OTHER INFORMATION: MYL2-r

<400> SEQUENCE: 8
cctctctgct tgtgtggtca                                                  20

<210> SEQ ID NO 9
<211> LENGTH: 20
<212> TYPE: DNA
<213> ORGANISM: Artificial Sequence
<220> FEATURE:
<223> OTHER INFORMATION: Atrogin 1-f

<400> SEQUENCE: 9
ttcagcagcc tgaactacga                                                  20

<210> SEQ ID NO 10
<211> LENGTH: 20
<212> TYPE: DNA
<213> ORGANISM: Artificial Sequence
<220> FEATURE:
<223> OTHER INFORMATION: Atrogin 1-r

<400> SEQUENCE: 10
tgaaagcttc ccccaaagta                                                  20

<210> SEQ ID NO 11
<211> LENGTH: 20
<212> TYPE: DNA
<213> ORGANISM: Artificial Sequence
<220> FEATURE:
<223> OTHER INFORMATION: MuRf1-f

<400> SEQUENCE: 11
tgaggtgcct acttgctcct                                                  20

<210> SEQ ID NO 12
<211> LENGTH: 20
<212> TYPE: DNA
<213> ORGANISM: Artificial Sequence
<220> FEATURE:
<223> OTHER INFORMATION: MuRf1-r

<400> SEQUENCE: 12
tcacctggtg gctattctcc                                                  20

<210> SEQ ID NO 13
<211> LENGTH: 20
<212> TYPE: DNA
<213> ORGANISM: Artificial Sequence
<220> FEATURE:
<223> OTHER INFORMATION: MSTN-f

<400> SEQUENCE: 13
acgctaccac ggaaacaatc                                                  20
```

```
<210> SEQ ID NO 14
<211> LENGTH: 20
<212> TYPE: DNA
<213> ORGANISM: Artificial Sequence
<220> FEATURE:
<223> OTHER INFORMATION: MSTN-r

<400> SEQUENCE: 14
ggagtcttga cgggtctgag                                         20
```